US008999332B2

(12) United States Patent
Sagi et al.

(10) Patent No.: US 8,999,332 B2
(45) Date of Patent: Apr. 7, 2015

(54) REGULATORS OF MMP-9 AND USES THEREOF

(71) Applicant: Yeda Research and Development Co. Ltd., Rehovot (IL)

(72) Inventors: Irit Sagi, Rehovot (IL); Gabriel Rosenblum, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/916,633

(22) Filed: Jun. 13, 2013

(65) Prior Publication Data

US 2013/0280247 A1  Oct. 24, 2013

Related U.S. Application Data

(63) Continuation of application No. 12/673,524, filed as application No. PCT/IL2008/001082 on Aug. 7, 2008, now abandoned.

(60) Provisional application No. 60/935,486, filed on Aug. 15, 2007.

(51) Int. Cl.
*A61K 39/395* (2006.01)
*C12N 9/64* (2006.01)
*A61K 38/00* (2006.01)

(52) U.S. Cl.
CPC .......... *A61K 39/3955* (2013.01); *C12N 9/6491* (2013.01); *C12Y 304/24035* (2013.01); *A61K 38/005* (2013.01); *C07K 2299/00* (2013.01)

(58) Field of Classification Search
None
See application file for complete search history.

(56) References Cited

U.S. PATENT DOCUMENTS

| | | |
|---|---|---|
| 2002/0159971 A1 | 10/2002 | Houde et al. |
| 2003/0157687 A1 | 8/2003 | Greene et al. |
| 2004/0175817 A1 | 9/2004 | Jepson et al. |
| 2006/0142749 A1 | 6/2006 | Ivkov |
| 2007/0172482 A1 | 7/2007 | Sagi et al. |

FOREIGN PATENT DOCUMENTS

| | | |
|---|---|---|
| EP | 2581445 | 4/2013 |
| WO | WO 97/00449 | 1/1997 |
| WO | WO 00/20860 | 4/2000 |
| WO | WO 03/006006 | 1/2003 |
| WO | WO 03/075765 | 9/2003 |
| WO | WO 2005/103071 | 11/2005 |
| WO | WO 2006/037513 | 4/2006 |
| WO | WO 2009/022328 | 2/2009 |

OTHER PUBLICATIONS

Communication Pursuant to Article 94(3) EPC dated Nov. 6, 2013 from the European Patent Office Re. Application No. 12198653.3.
Decision on Rejection Dated Feb. 13, 2014 From the State Intellectual Property Office of the People's Republic of China Re. Application No. 200880112385.3 and Its Translation Into English.
Official Decision of Rejection Dated Feb. 21, 2014 From the Japanese Patent Office Re. Application No. 2010-520682 and Its Translation into English.
Delacourt et al. "Imbalance Between 95 kDa Type IV Collagenase and Tissue Inhibitor of Metalloproteinases in Sputum of Patients With Cystic Fibrosis", American Journal of Respiratory and Critical Care Medicine, 152(2): 765-774, Aug. 1995.
Sorbi et al. "Elevated Levels of 92-KD Type IV Collagenase (Matrix Metalloproteinase 9) in Giant Cell Arteritis", Arthritis & Rheumatism, 39(10): 1747-1753, Oct. 1996.
Vadillo-Ortega et al. "92-KD Type IV Collagenase (Matrix Metalloproteinase-9) Activity in Human Amniochorion Increases With Labor", American Journal of Pathology, 146(1): 148-156, Jan. 1995.
Communication Pursuant to Article 94(3) EPC Dated May 27, 2011 From the European Patent Office Re. Application No. 08789758.3.
European Search Report and the European Search Opinion Dated Mar. 19, 2013 From the European Patent Office Re. Application No. 12198653.3.
International Preliminary Report on Patentability Dated Feb. 25, 2010 From the International Bureau of WIPO Re.: Application No. PCT/IL2008/001082.
International Search Report Dated Dec. 22, 2008 From the International Searching Authority Re.: Application No. PCT/IL08/01082.
Office Action Dated Dec. 5, 2011 From the Israel Patent Office Re. Application No. 203788 and Its Translation Into English.
Official Action Dated Dec. 13, 2012 From the US Patent and Trademark Office Re. U.S. Appl. No. 12/673,524.
Patent Examination Report Dated Sep. 4, 2012 From the Australian Government, IP Australia Re. Application No. 2008288082.
Request for Examination Dated Mar. 17, 2012 From the Federal Service of Intellectual Property, Federal State Budget Institute, Federal Institute of Industrial Property of the Russian Federation Re. Application No. 2010108429 and Its Summary in English.
Supplementary European Search Report and the European Search Opinion Dated Jul. 14, 2010 From the European Patent Office Re. Application No. 08789758.3.
Translation of Notice of Reason for Rejection Dated Feb. 5, 2013 From the Japanese Patent Office Re. Application No. 2010-520682.
Translation of Search Report Dated Oct. 23, 2012 From the State Intellectual Property Office of the People's Republic of China Re. Application No. 200880112385.3.
Written Opinion Dated Dec. 22, 2008 From the International Searching Authority Re.: Application No. PCT/IL08/01082.
Atkinson et al. "Matrix Metalloprotease-9 in Lung Remodeling", American Journal of Respiratory, Cellular and Molecular Biology, 28(1): 12-24, Jan. 2003.
Borkakoti "Matrix Metalloproteases: Variations on a Theme", Progress in Biophysics & Molecular Biology, 70(1): 73-94, 1998.
Borkakoti et al. "CD Molecule—Adhesion Molecule—Extracellular Matrix", SIGMA Antibody Catalog, p. 380, 2001.

(Continued)

*Primary Examiner* — Sheela J Huff

(57) ABSTRACT

A method of regulating an activity of metalloproteinase 9 (MMP-9) is disclosed. The method comprises contacting the MMP-9 with an agent which specifically interacts with an OG domain of the MMP-9. Molecules capable of specifically interacting with the OG domain, methods of identifying same, pharmaceutical compositions comprising same and uses thereof are also disclosed.

2 Claims, 7 Drawing Sheets
(7 of 7 Drawing Sheet(s) Filed in Color)

(56) References Cited

OTHER PUBLICATIONS

Buras et al. "Animal Models of Sepsis: Setting the Stage", Nature Reviews: Drug Discovery, 4: 854-866, Oct. 2005.
Cha et al. "Structural Basis of the Adaptive Molecular Recognition by MMP9", Journal of Molecular Biology, 320: 1065-1079, 2002.
DePristo et al. "Ab Initio Construction of Polypeptide Fragments: Efficient Generation of Accurate, Representative Ensembles", Proteins: Structure, Function, and Genetics, 51: 41-55, 2003.
Dermer "Another Anniversary for the War on Cancer", Bio/Technology, 12: 320, Mar. 1994.
Emonard et al. "Low Density Lipoprotein Receptor-Related Protein Mediates Endocytic Clearance of Pro-MMP-2-TIMP-2 Complex Through A Thrombospondin-Independent Mechanism", The Journal of Biological Chemistry, 279(52): 54944-54951, Dec. 24, 2004.
Freshney "Introduction", Culture of Animal Cells, A Manual of Basic Technique, p. 3-4, 1983.
Galluzzi et al. "Modern Care Patients With Alzheimer Disease: Rationale for Early Intervention", Journal of the American Osteopathology Association, 110(9/Suppl.8): S37-S42, Sep. 2010.
Gura "Systems for Identifying New Drugs Are Often Faulty", Science, 278: 1041-1042, Nov. 7, 1997.
Jain "Barriers to Drug Delivery in Solid Tumors. Many Tumors Resist Full Penetration by Anticancer Agents. Such Resistance May Help Explain Why Drugs That Eradicate Tumor Cells in Laboratory Dishes Often Fail to Eliminate Malignancies in the Body", Scientific American, 271: 58-65, Jul. 1994.
Martens et al. "A monoclonal Antibody Inhibits Gelatinase B/MMP-9 by Selective Binding to Part of the Catalytic Domain and Not to the Fibronectin or Zinc Binding Domains", Biochimica et Biophysica Acta, BBA, 1770(2): 178-186, Feb. 2007. Abstract Only.
Maskos "Crystal Structures of MMPs in Complex With Physiological and Pharmacological Inhibitors", Biochimie, 87: 249-263, 2005.
Opdenakker et al. "Functional Roles and Therapeutic Targeting of Gelatinase B and Chemokines in Multiple Sclerosis", The Lancet Neurology, 2: 747-756, 2003.
Rittirsch et al. "The Disconnect Between Animal Models of Sepsis and Human Sepsis", Journal of Leukocyte Biology, 81: 137-143, Jan. 2007.
Rosenblum et al. "Insights Into the Structure and Domain Flexibility of Full-Length Pro-Matrix Metalloproteinase-9/Gelatinase B", Structure, XP022368313, 15(10): 1227-1236, Oct. 16, 2007.
Schaeffer et al. "Improving the Accuracy of PSI-BLAST Protein Database Searches With Composition-Based Statistics and Other Refinements", Nucleic Acids Research, 29(14): 2994-3005, 2001.
Stetler-Stevenson et al. "Tumor Cell Interactions With the Extracellular Matrix During Invasion and Metastasis", Annual Review in Cell Biology, 9: 541-573, 1993.
Svergun "Determination of the Regularization Parameter in Indirect-Transform Methods Using Perceptual Criteria", Journal of Applied Crystallography, 25: 495-503, 1992.
Van den Steen et al. "The Hemopexin and O-Glycosylated Domains Tune Gelatinase B/MMP-9 Bioavailability Via Inhibition and Binding to Cargo Receptors", The Journal of Biological Chemistry, XP002588835, 281(27): 18626-18637, Jul. 7, 2006. p. 18629, § 4, p. 18632, § 5 - p. 18633, § 1, Table 1, Fig.4, p. 18632-18633.
Watanabe et al. "Real-Time Dual Zumographic Analysis of Matrix Metalloproteinases Using Fluorescein-Isothiocyante-Labed Gelatin and Texas-Red-Labeled Casein", Analytical Biochemistry, 307: 390-392, 2002.
Winter et al. "Humanized Antibodies", Immunology Today, 14(6): 243-246, 1993.
Translation of Office Action Dated Jun. 28, 2013 From the State Intellectual Property Office of the People's Republic of China Re. Application No. 200880112385.3.
Translation of Search Report Dated Jun. 28, 2013 From the State Intellectual Property Office of the People's Republic of China Re. Application No. 200880112385.3.
Translation of Notice of Reason for Rejection Dated Jul. 2, 2013 From the Japanese Patent Office Re. Application No. 2010-520682.
Office Action Dated Feb. 27, 2014 From the Israel Patent Office Re. Application No. 222302 and Its Translation Into English.
Examination Report Dated May 23, 2014 From the Government of India, Patent Office, Intellectual Property Building Re.: Application No. 464/MUMNP/2010.

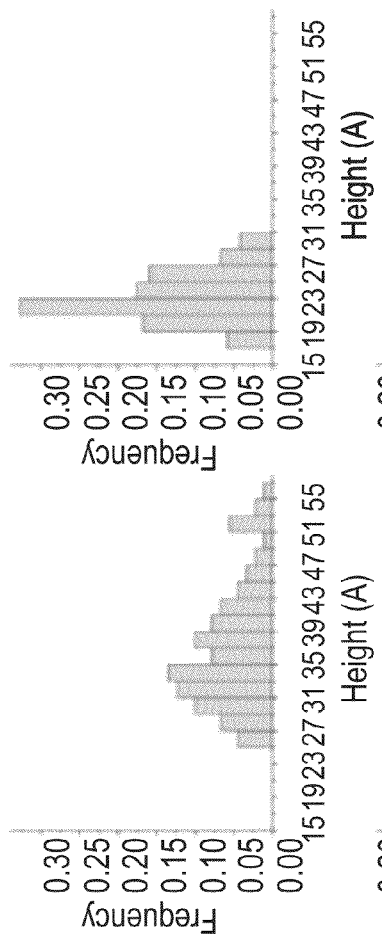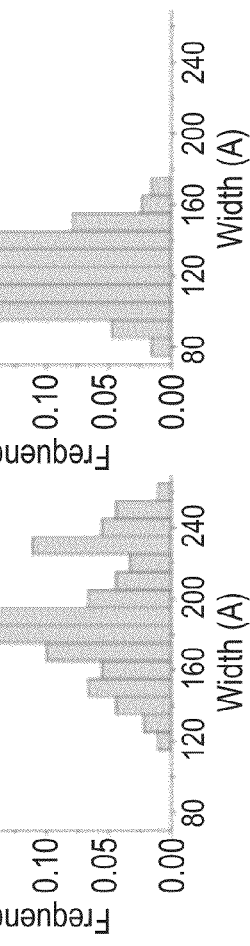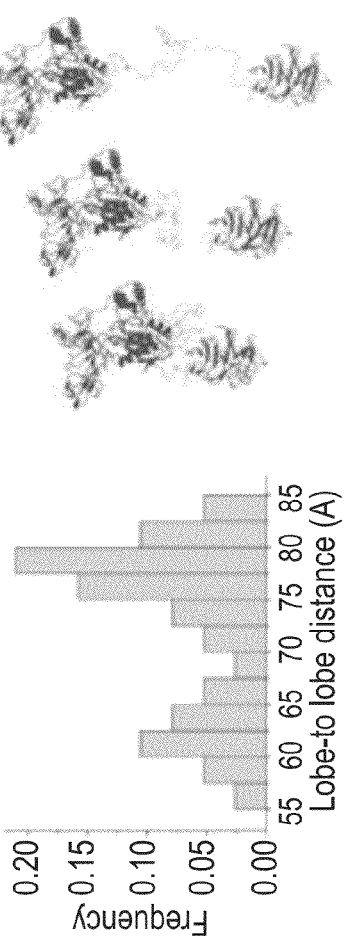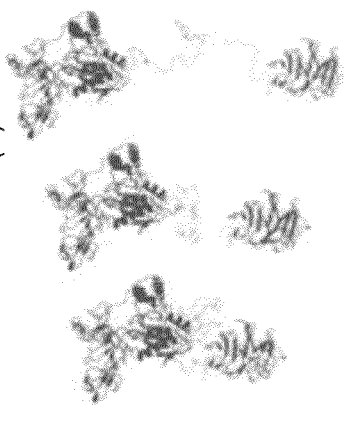
FIG. 4A  FIG. 4B  FIG. 4C  FIG. 4D  FIG. 4E  FIG. 4F

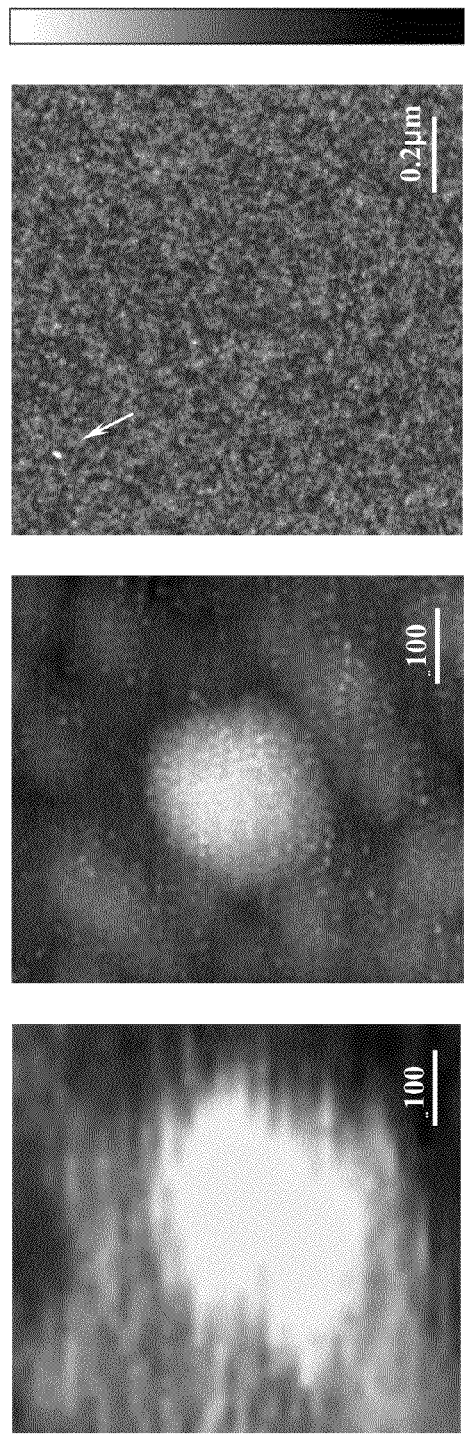

REGULATORS OF MMP-9 AND USES THEREOF

RELATED APPLICATIONS

This application is a continuation of U.S. patent application Ser. No. 12/673,524 filed on Nov. 18, 2010, which is a National Phase of PCT Patent Application No. PCT/IL2008/001082 having International filing date of Aug. 7, 2008, which claims the benefit of priority of U.S. Provisional Patent Application No. 60/935,486 filed on Aug. 15, 2007. The contents of the above applications are all incorporated herein by reference.

FIELD AND BACKGROUND OF THE INVENTION

The present invention relates to regulators of MMP-9 and, more particularly, to regulators targeted towards the OG domain thereof.

The physiological and pathological roles of matrix metalloproteinases (MMPs) are versatile. Members of the MMP family have been implicated in numerous aspects of the migration of inflammatory and cancer cells through connective tissues, not only by catabolizing extracellular matrix (ECM) components but also by processing various soluble mediators, promoting many disease states. Although all MMPs share similar catalytic sites, marked differences are observed in their substrate specificity, at least in part due to the presence of additional substrate binding sites in non-catalytic protein domains. As a consequence, different MMPs have different biological functions. MMP-9, also known as gelatinase B, is a prototypical target in inflammatory diseases, because of its tissue-damaging roles and inflammation-promoting processing of soluble proteins, including protease inhibitors, chemokines and cytokines.

In contrast, MMP-2 or gelatinase A has mainly anti-inflammatory and homeostatic functions, presumably by the inactivation of inflammatory chemokines and by regulating connective tissue turn-over. This implies that selective inhibitors, discriminating between these highly similar enzymes, are crucial for efficient anti-inflammatory therapy without side-effects. In this perspective, other non-catalytic parts of the enzyme, differentiating MMP-2 and MMP-9, may be targeted to generate selective inhibitors.

Interestingly, the main structural difference between MMP-9 and MMP-2 is the presence of an extensively O-glycosylated (OG) domain in MMP-9 [Opdenakker, G., et al (2001), Trends Immunol. 22, 571-579; Van den Steen, P. E., et al (2006) J Biol Chem. 281, 18626-18637]. Other domains in MMP-9 are also found in MMP-2 and include a pro-peptide domain responsible for maintaining latency, a catalytic domain in which three fibronectin repeats are inserted, and a C-terminal domain also known as the hemopexin-like domain which constitutes an exosite for binding of the endogenous MMP-9 and MMP-2 inhibitor, tissue inhibitor of metalloproteinase 1 (TIMP-1). Despite its great importance in many disease states and in contrast to MMP-2, the available structural information about MMP-9 is limited to its two terminal domains, rather than the full length enzyme. The X-ray structure of the N-terminal part [Elkins et al, 2002, Acta Crystallogr D Biol Crystallogr 58, 1182-1192], containing the pro-catalytic domain shows that it possesses a matrixin fold. The C-terminal hemopexin-like domain consists of a four-bladed β-propeller structure with pseudo-four-fold symmetry [Cha et al, 2002, J Mol Biol 320, 1065-1079]. FIG. 1A presents the crystal structures of the pro-catalytic and the hemopexin-like domains of pro-MMP-9. The domains are connected by a dotted line representing the 64 amino acid-long linker (containing 22 proline residues, 6 glycine residues and approximately 12-14 O-linked glycans [Van den Steen et al., 2001, Biochim Biophys Acta 1528, 61-73]. Importantly, the linker domain of pro-MMP-9 is 2-3 times longer than linker regions of collagenases, stromelysins and gelatinase A, of the MMP family, for which typical linker lengths span a range of only 21-27 amino acid residues.

Crystallization of the linker domain in pro-MMP-9 separately or together with other protein domains has proven difficult. The lack of a large side chain in the case of glycine and the presence of a built-in bend in the case of proline interfere with the formation of secondary structure and often result in loops or unstructured regions. In addition, the presence of clustered serines and threonines as attachment points for O-glycans might yield steric effects that could hinder crystallographic packing. This domain has also been termed the collagen V-like domain, due to its sequence similarity to collagen V and has recently been renamed O-glycosylated (OG) domain. The OG domain is active in the orientation of the hemopexin domains to enable exosite interactions. However, nothing is known of the influence of the OG domain on the overall 3D structure of MMP-9 and its biophysical nature.

U.S. Patent No. 20040175817 teaches identification of MMP-9 modulators based on the crystal structure of its catalytic subunit. However, since MMPs in general share a high sequence homology in their catalytic sites, modulators designed to target the catalytic site will not be selective towards MMP-9.

SUMMARY OF THE INVENTION

There is a need for MMP-9 specific regulators. According to one aspect, there is provided a method of regulating an activity of metalloproteinase 9 (MMP-9), the method comprising contacting the MMP-9 with an agent which specifically interacts with an OG domain of the MMP-9, thereby regulating the activity of MMP-9.

According to another aspect, there is provided a method of identifying an agent capable of specifically regulating MMP-9, the method comprising determining whether the agent is capable of interacting with an OG domain of MMP-9, the agent being a putative MMP-9 specific regulator.

According to yet another aspect, there is provided a method of treating a MMP-9 mediated medical condition, the method comprising administering to a subject in need thereof a therapeutically effective amount of an agent which specifically interacts with an OG domain of MMP-9, thereby treating the MMP-9 mediated disease or condition.

According to still another aspect, there is provided a molecule capable of specifically regulating an activity of MMP-9, wherein the molecule interacts with an OG domain of the MMP-9, with the proviso that the molecule is not a non-humanized antibody.

According to an additional aspect, there is provided a humanized antibody comprising an antigen recognition domain which specifically interact with an OG domain of MMP-9.

According to yet an additional aspect, there is provided a pharmaceutical composition comprising as an active ingredient a molecule capable of specifically regulating an activity of MMP-9, wherein the molecule interacts with an OG domain of the MMP-9, with the proviso that the molecule is not a non-humanized antibody and a pharmaceutically acceptable carrier.

According to an embodiment, the MMP-9 is native MMP-9.

According to yet another embodiment, the activity is a collagenolytic activity.

According to yet another embodiment, the activity is a gelatinolytic activity.

According to yet another embodiment, the regulating is up-regulating.

According to yet another embodiment, the regulating is down-regulating.

According to yet another embodiment, the agent comprises a polypeptide agent.

According to yet another embodiment, the polypeptide agent comprises an antibody.

According to yet another embodiment, the agent comprises a small molecule.

According to yet another embodiment, the determining is effected by comparing a structure of the agent to a structure of an OG domain of MMP-9.

According to yet another embodiment, the determining is effected by contacting said agent with an isolated OG domain of MMP-9.

According to yet another embodiment, the agent comprises a polypeptide.

According to yet another embodiment, the polypeptide comprises an antibody.

According to yet another embodiment, the agent comprises a small molecule.

According to yet another embodiment, the agent is identified as described herein.

According to yet another embodiment, the agent comprises a small molecule or a polypeptide agent.

According to yet another embodiment, the polypeptide agent comprises an antibody.

According to yet another embodiment, the molecule comprises a humanized antibody comprising an antigen recognition domain which specifically interacts with the OG domain of MMP-9.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
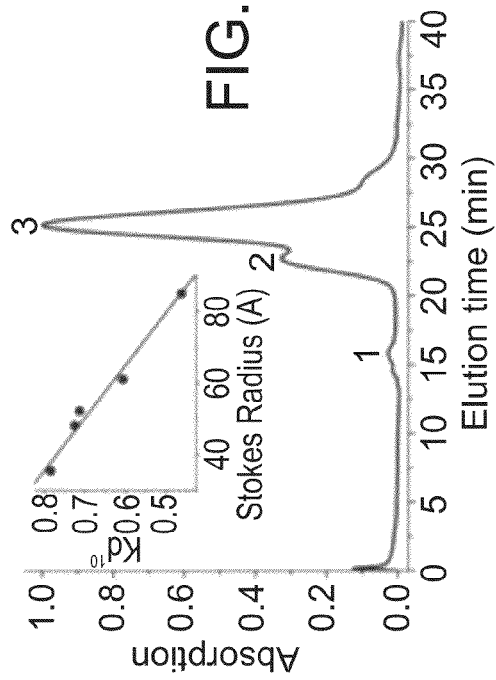
Figure 1B:
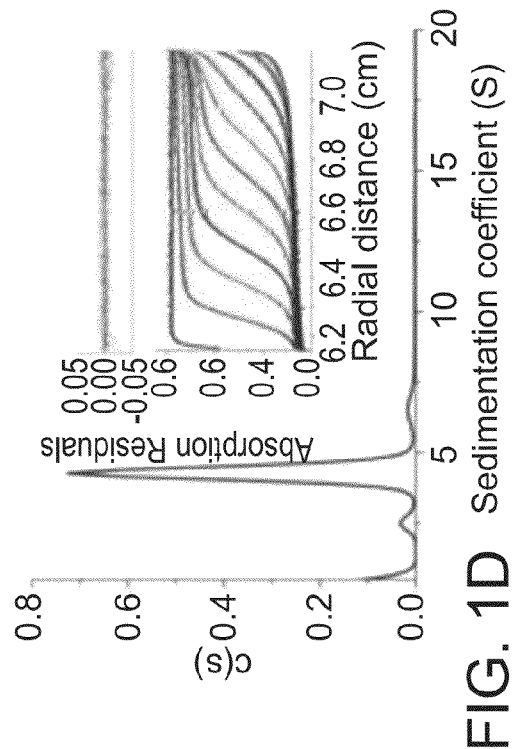
Figure 1C:
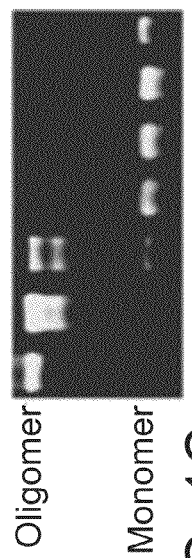
Figure 1D:

FIGS. 1A-D are computer generated models and graphs characterizing pro-MMP-9. FIG. 1A illustrates the crystal structures of the terminal domains. The N-terminal domain of pro-MMP-9 (PDB code: 1L6J) is comprised of the pro-peptide (green), three fibronectin type-II repeats (blue) and catalytic domain (red) with the zinc-containing active site (gray sphere). The OG domain (dashed line) contains a 64 residue-fragment of unknown structure and it connects the N-terminal domain to the C-terminal haemopexin-like domain (PDB code: 1ITV), which consists four propeller blades (cyan). FIG. 1B is a graph illustrating the size exclusion chromatography showing the elution profile of oligomeric species (peak 1, 15.8 min and peak 2, 22.7 min) and monomeric (peak 3, 25.1 min) forms of pro-MMP-9. Inset: Porath plot [57] of protein standards with known Stokes radii were used to calibrate the superdex 200 column (from left to right: thyroglobulin 85 Å, ferritin 61 Å, catalase 52.2 Å, aldolase 48.1 Å, albumin 35.5 Å). The cubic root of Kd is plotted against the Stokes radius of each protein, and linear least-square fit is shown. FIG. 1C is a photograph of a gelatin zymogram. Glycerol sedimentation was applied in order to separate monomers from higher oligomeric structures in preperative amounts. Aliquots from each fraction were assayed in a gelatin zymogram. High oligomeric structures are present in fractions 1-3. Fraction 3 contained a mixture of all oligomeric forms. Fractions 4-7 contained mostly the monomeric form. FIG. 1D is an analytical ultracentrifugation sedimentation velocity analysis, used to calculate the distribution of sedimentation coefficient. Inset: modeling the sedimentation profiles (lines) from the experimental data (dots) as a function of time and distance from the axis of rotation. Residuals plot is shown in the upper panel. For clarity, only every tenth profile used in the analysis is shown.

Figure 2B:
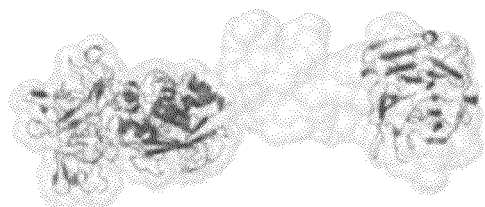
Figure 2E:
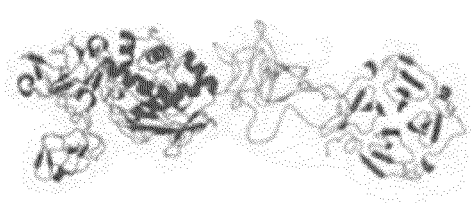
Figure 2A:
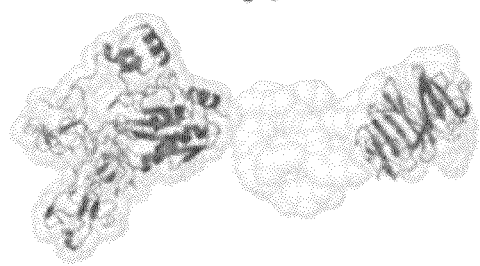
Figure 2C:
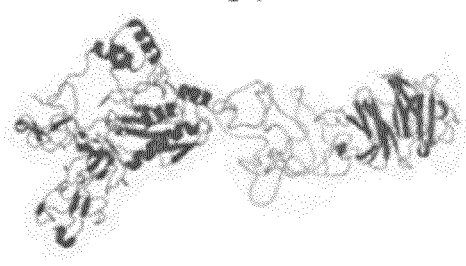
Figure 2D:
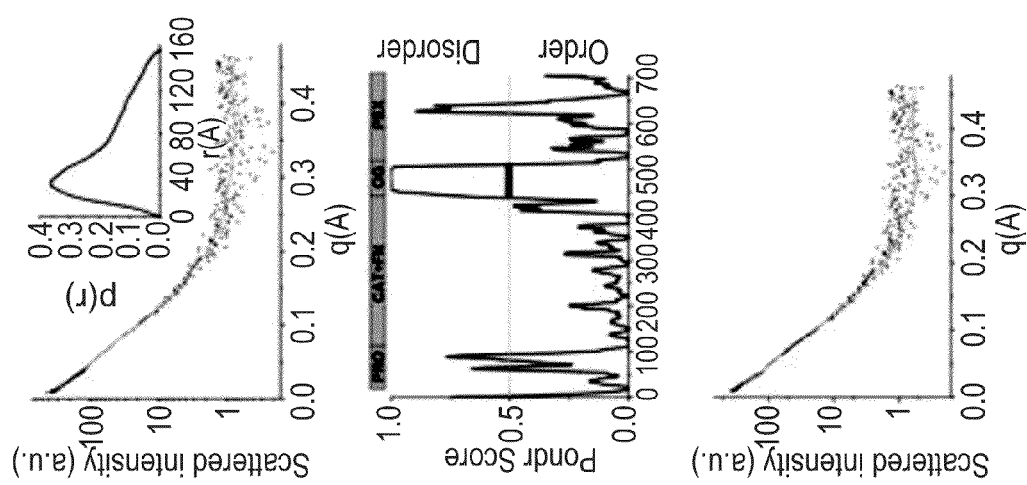

FIGS. 2A-E are computer generated models and graphs illustrating the structural analysis of pro-MMP-9. FIG. 2A is a graph illustrating SAXS data of pro-MMP-9 in solution. Experimental X-ray intensity data (black dots) are compared with the most probable model (gray line) using CHADD. Inset: pair distribution function of the experimental SAXS data. FIG. 2B illustrates Pro-MMP-9 models reconstructed by CHADD. The models obtained from the SAXS data are represented by white spheres with a radius of 5 Å. Each model was rotated at 0° and 90° along the vertical axis. The docked crystal structures of the N- and C-terminal domains [22, 24] are represented as blue and red ribbons, respectively. FIG. 2C is a prediction of a long-disorder region (thick black line) by PONDR [37] in the sequence of pro-MMP-9 and the corresponding domain organization (top bar: PRO-pro-peptide, CAT+FN—catalytic domain and three fibronectin type-II repeats, OG-O-glycosylated domain, PEX—hemopexin-like domain). FIG. 2D illustrates the fitting of the calculated scattering curve of the full-length pro-MMP-9 with the reconstructed OG domain, to the experimental data. The calculated curves of the best three models are shown in green, cyan and yellow lines. The experimental data is represented as black dots. The three best models of the OG domain were calculated using RAPPER [38, 39] within the CHADD model. FIG. 2E illustrates the structural reconstruction of the OG domain. The best three models are shown in ribbon representation colored green, cyan and yellow.

Figure 3D:
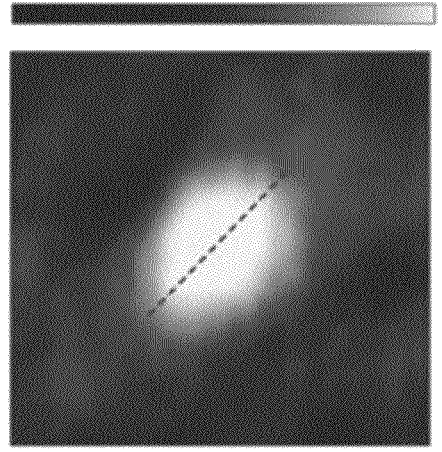
Figure 3E:
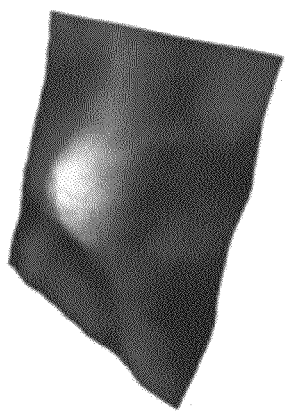
Figure 3F:
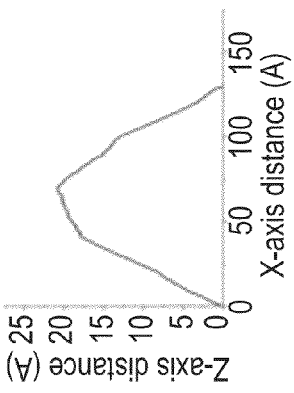
Figure 3A:
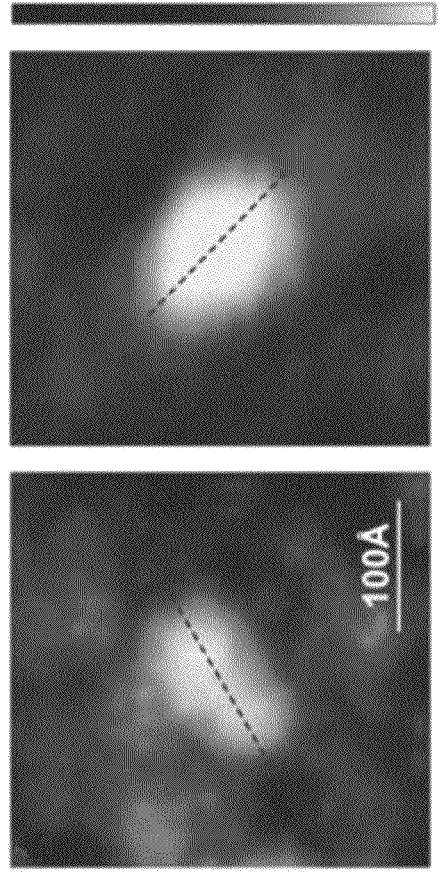
Figure 3B:
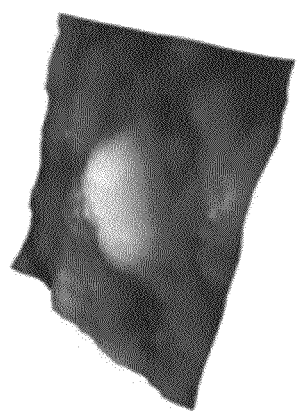
Figure 3C:
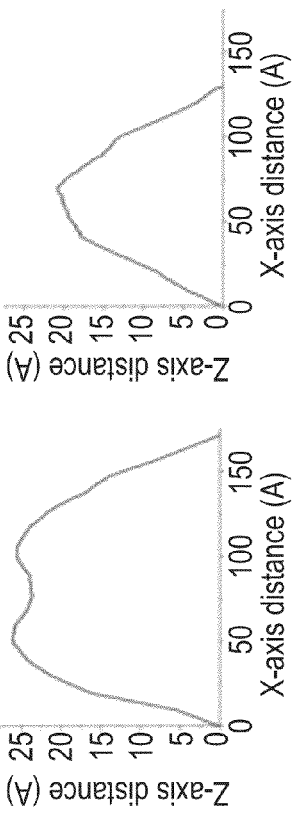

FIGS. 3A-F are graphs and AFM images of wild-type and mutated pro-MMP-9. Glutaraldehyde served as covalent linker between the amine on the surface to the protein. All scans employed a spike tip. FIGS. 3A-C): Semi-dry mode scans of wild-type pro-MMP-9. FIGS. 3D-F: Semi-dry mode scan of pro-MMP-9ΔOG mutant. FIG. 3A and FIG. 3D are 2D representation. FIG. 3B and FIG. 3E are 3D representation. FIG. 3C and FIG. 3F are XZ cross-sections along the dashed line shown in FIG. 3A and FIG. 3D. For sample preparation and imaging conditions, see text. Height scale is indicated by the bar to the right in which the Z-axis ranges from 0 to 50 Å (dark to light).

FIGS. 4A-F are size distribution histograms of the wild type (left) and pro-MMP-9ΔOG (right) as measured by AFM.

The y-axis of all histograms is the normalized frequency obtained by dividing the counts by the total population. FIGS. 4A and 4B—height distribution. FIGS. 4C and 4D—width distribution. The width values were corrected as described in the experimental procedures section. FIG. 4E illustrates the lobe-to-lobe distribution of wild type pro-MMP-9. The separation between lobes in pro-MMP-9ΔOG could not be resolved. FIG. 4F illustrates the modeling conformational states of pro-MMP-9. A standard deviation of 9.5 Å, as calculated according to the lobe-to-lobe AFM data was subtracted (left), or added (right) to the inter-domain separation of the averaged structure (middle) obtained by SAXS structural reconstruction. The N- and C-terminal domains [22, 24] are represented by blue and red cartoon, respectively. The OG domain was reconstructed by RAPPER [38, 39], and is represented by green Cα trace.

Figures 5A, 5B:

FIGS. 5A-B illustrate reconstructed pro-MMP-9 models obtained by SAXS. FIG. 5A is a GASBOR model. FIG. 5B is a CHADD model. White spheres with a radius of 5 Å represent the obtained models. The docked crystal structures of the N- and C-terminal domains are represented as blue and red cartoons, respectively. Each model was rotated at 0° and 90° along the vertical axis.

FIGS. 6A-C are AFM images of pro-MMP-9. Glutaraldehyde served as a covalent linker between the amine on the surface to the protein. All scans employed a spike tip, except for that of FIG. 6A which used an oxide-sharpened silicon nitride tip. FIG. 6A: Wild type pro-MMP-9 under buffer solution. FIG. 6B: Dessicated sample of the wild-type enzyme scanned in ambient conditions. FIG. 6C: Blank sample subjected to the same immobilization procedure without applying the enzyme. The arrow indicates a single particle observed on 1×1 μm² scan. Height scale is indicated by the bar to the right in which the Z-axis ranges from 0 to 50 Å (dark to light).

Figure 7B:
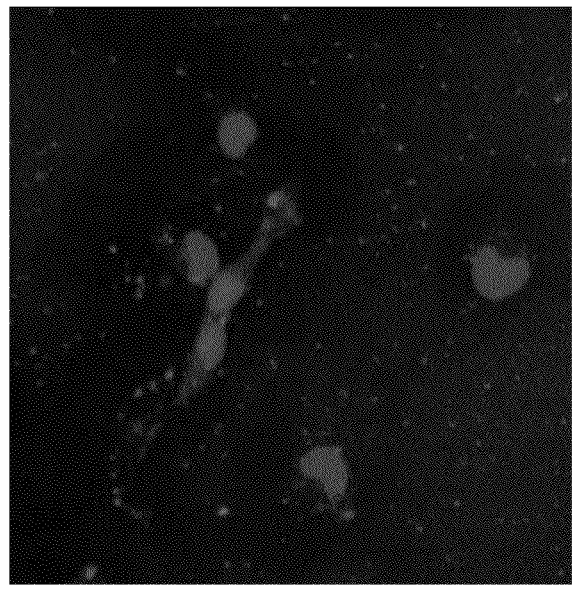
Figure 7A:
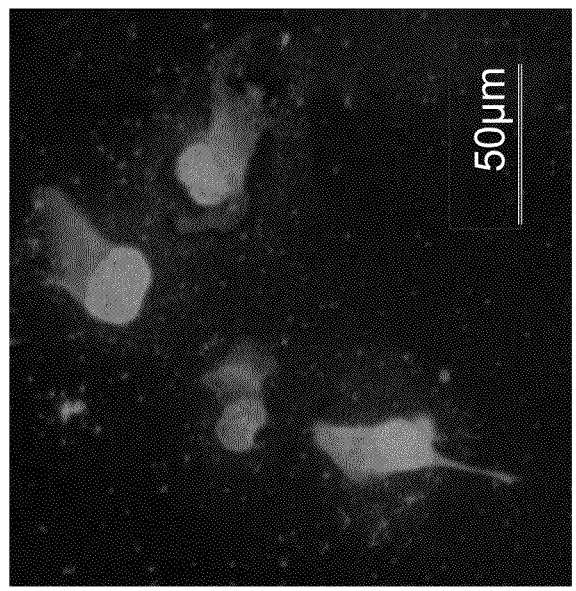

FIGS. 7A-B: FIG. 7A illustrates in situ zymography of HT1080 cells expressing secreted MMP-9. Detection of green fluorescence is indicative of proteolytic activity of collagen type IV. Blue indicates nuclear staining (Hoechst). FIG. 7B illustrates the incubation of HT1080 cells with Anti-MMP (9 hr) and then overlayed with collagen type-IV conjugated to Oregon green. Lack of pronounced green fluorescence around the cells indicates inhibition of pericellular proteolysis by MMP-9.

DESCRIPTION OF THE PREFERRED EMBODIMENTS

The present invention relates to regulators of MMP-9 and, more particularly, to regulators targeted towards the OG domain thereof.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Members of the metalloproteinase (MMP) family have been implicated in numerous aspects of the migration of inflammatory and cancer cells through connective tissues, promoting many disease states. Although all MMPs share similar catalytic sites, their substrate binding sites differ. As a consequence, different MMPs have different biological functions. For example, MMP-9 promotes tissue damage and inflammation, whereas MMP-2 comprises mainly anti-inflammatory and homeostatic functions. This implies that selective inhibitors, discriminating between these highly similar enzymes, are crucial for efficient anti-inflammatory therapy without side-effects.

Whilst conceiving the invention, the present inventors have come to the understanding that the main structural difference between MMP-9 and MMP-2 is the presence of an extensively O-glycosylated (OG) domain in MMP-9. However, the available structural information about MMP-9 is limited to its two terminal domains, which does not include this OG domain. As such, there is no information pertaining to the influence of the OG domain on the overall 3D structure of MMP-9 and its biophysical nature.

Whilst reducing the present invention to practice, the present inventors have performed a novel structural analysis combining small-angle X-ray scattering (SAXS) with single molecule atomic force microscopy (AFM) imaging to characterize the first full-length structure of pro-MMP-9 and the molecular character of its O-glycosylated linker domain. SAXS followed by image and structural reconstruction analyses provided the molecular shape of full-length pro-MMP-9 representing its averaged conformation in solution (FIGS. 2A-E). This structure, which is supported by high-resolution AFM imaging (FIGS. 3A-F and 4A-E) and biophysical measurements, shows an elongated protein with the OG domain acting as a flexible 30 Å long linker between the two terminal domains (FIGS. 5A-B). The degree of the OG domain flexibility was statistically evaluated from the various protein conformations detected by single molecule imaging (FIG. 4F). The full-length structural-dynamic model of pro-MMP-9 provides novel insights into the role of protein domain flexibility in the regulation of recognition, binding and processing of substrates, ligands and receptors, required for MMP-9 activities.

Whilst further reducing the present invention to practice, the present inventors showed by in-situ zymography that an antibody capable of specifically interacting with the OG domain of MMP-9, blocks the collagenolytic activity therof, but not the gelatinolytic activity thereof (FIGS. 7A-B). Thus, the present inventors suggest that use of agents that regulate the OG domain flexibility may be used to control the pathological activities of this enzyme.

Thus, according to an aspect of the invention, there is provided a method of regulating an activity of metalloproteinase 9 (MMP-9), the method comprising contacting the MMP-9 with an agent which specifically interacts with an OG domain of the MMP-9, thereby regulating the activity of MMP-9.

As used herein, the term "MMP-9" (Multidomain zinc endopeptidase matrix metalloproteinase-9, also named gelatinase B) refers to the precursor or active forms of the mammalian (e.g., human) MMP-9 polypeptide, (EC 3.4.24.35; Swiss Prot No. P14780) including homologs, orthologs and isoforms thereof. MMP-9 typically comprises three domains—a catalytic domain, a substrate binding domain and a linker domain therebetween. The linker domain, also referred to herein as the collagen V-like domain or the O-glycosylated (OG) domain comprises 64 amino acids, 22 of which are proline residues, 6 of which are glycine residues and approximately 12-14 O-linked glycans.

According to an embodiment of this aspect of the invention, the MMP-9 is native i.e. not denatured. According to another embodiment of this aspect of the invention, the MMP-9 is active, preferably fully active.

Activities of MMP-9 include, but are not limited to, gelatinolytic activities, degradation of native collagens of type I, III and XI (collagenolytic acitivities), degradation of elastin, aggrecan, the laminin A chain and myelin basic protein.

The term "regulating" as used herein refers to down-regulating or up-regulating. It will be appreciated that agents which inhibit the flexibility of the OG domain will down-regulate a function of MMP-9 that require the OG domain to be flexible, such as its collagenolytic activity. In contrast, activities which require a particular 3D structure of MMP-9 and do not require flexibility of the OG domain may be up-regulated by agents interacting with the OG domain. An example of such an activity is its gelatinolytic activity or an ability to interact with receptors and/or growth factors.

As mentioned, the method of the invention is effected by contacting MMP-9 with an agent capable of specifically interacting with its OG domain.

As used herein, the term "contacting" refers to enabling MMP-9 to come into contact with the agent under conditions (i.e. time, temperature, buffer) that allow the agent to interact with its OG domain (e.g. bind to the OG domain) and affect rigidity thereof. It will be appreciated that the contacting may be effected in vivo, ex vivo or in vitro.

The phrase "specifically interacting", as used herein refers to both an enhanced affinity towards the OG domain of MMP-9 as opposed to another domain of MMP-9 (e.g. catalytic domain or substrate binding domain) and an enhanced affinity towards the OG domain of MMP-9 over an OG domain of another metalloproteinase enzyme e.g. MMP-2. An example of minimal affinity is probably $10^{-5}$M. Preferably the agent interacts with the MP-9 OG domain with at least 3 times higher affinity as compared to the above, more preferably, with at least 5 times higher affinity, more preferably with at least 10 times higher affinity or greater. It will be appreciated that since the amino acid sequence of the MMP-9 OG domain is specific to MMP-9 (as opposed to the amino acid sequence of the catalytic domain which is highly homologous between MMP-9 and MMP-2), agents capable of specifically interacting with the MMP-9 OG domain are thus capable of specifically regulating MMP-9.

Agents (i.e. molecules) contemplated by the present invention capable of interacting with the OG domain of MMP-9 include, but are not limited to polypeptide agents (e.g. antibodies comprising an antigen recognition domain which specifically interact with an OG domain of MMP-9), peptides and small molecules. It will be appreciated that the agents may interact with the OG domain based on specific amino acid sequence recognition and/or conformational recognition.

Antibody agents that recognize the OG domain of MMP-9 are commercially available, e.g., from Sigma, Chemicon and Abcam.

The term "antibody" as used in this invention includes intact molecules as well as functional fragments thereof, such as Fab, F(ab')2, and Fv that are capable of binding to the specific mitochondrial proteins. Smaller antibody fragments may be advantageous over whole antibodies since they are able to penetrate tissue more readily and are more rapidly cleared from the body. This is especially relevant for the in-vivo use of MMP-9 specific antibodies. Also, an additional advantage of antibody fragments is that they may be produced in bacteria or yeasts.

Generation of antibodies directed against the OG domain of MMP-9 may be effected by using a peptide which comprises the OG domain. The antibody may be selected using other MMP-9 domains as negative controls.

Suitable Antibody fragments for practicing the present invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single chain Fv ("scFv"), a genetically engineered single chain molecule including the variable region of the light chain and the variable region of the heavy chain, linked by a suitable polypeptide linker.

(iii) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(iv) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds).

Methods of generating antibodies (i.e., monoclonal and polyclonal) are well known in the art. Antibodies may be generated via any one of several methods known in the art, which methods can employ induction of in-vivo production of antibody molecules, screening of immunoglobulin libraries (Orlandi D. R. et al., 1989. Proc. Natl. Acad. Sci. U.S.A. 86:3833-3837; Winter G. et al., 1991. Nature 349:293-299) or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler G. et al., 1975. Nature 256:495-497; Kozbor D. et al., 1985. J. Immunol. Methods 81:31-42; Cote R J. et al., 1983. Proc. Natl. Acad. Sci. U.S.A. 80:2026-2030; Cole S P. et al., 1984. Mol. Cell. Biol. 62:109-120).

In cases where target antigens are too small to elicit an adequate immunogenic response when generating antibodies in-vivo, such antigens (haptens) can be coupled to antigenically neutral carriers such as keyhole limpet hemocyanin (KLH) or serum albumin [e.g., bovine serum albumine (BSA)] carriers (see, for example, U.S. Pat. Nos. 5,189,178 and 5,239,078]. Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. [(see, for example, Harlow and Lane, "Antibodies: A Laboratory Manual", Cold Spring Harbor Laboratory, New York, (1988)]. For example, antibody fragments according to the present invention can be prepared by proteolytic hydrolysis of the antibody or by expression in E. coli or mammalian cells (e.g., Chinese hamster ovary cell culture or other protein expression systems) of DNA encoding the fragment.

Alternatively, antibody fragments can be obtained by pepsin or papain digestion of whole antibodies by conventional methods. As described hereinabove, an (Fab')2 antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: Goldenberg, U.S. Pat. Nos. 4,036,945 and 4,331,647; Porter, R R., 1959. Biochem. J. 73:119-126). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

As described hereinabove, an Fv is composed of paired heavy chain variable and light chain variable domains. This association may be noncovalent (see, for example, Inbar et al., 1972. Proc. Natl. Acad. Sci. USA. 69:2659-62). Alternatively, as described hereinabove the variable domains can be linked to generate a single chain Fv by an intermolecular disulfide bond, or alternately, such chains may be cross-linked by chemicals such as glutaraldehyde.

Preferably, the Fv is a single chain Fv.

Single chain Fv's are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. Ample guidance for producing single chain Fv's is provided in the literature of the art (for example, refer to: Whitlow and Filpula, 1991. Methods 2:97-105; Bird et al., 1988. Science 242:423-426; Pack et al., 1993. Bio/Technology 11:1271-77; and Ladner et al., U.S. Pat. No. 4,946,778).

Isolated complementarity determining region peptides can be obtained by constructing genes encoding the complementarity determining region of an antibody of interest. Such genes may be prepared, for example, by RT-PCR of mRNA of an antibody-producing cell. Ample guidance for practicing such methods is provided in the literature of the art (for example, refer to Larrick and Fry, 1991. Methods 2:106-10).

It will be appreciated that for human therapy, humanized antibodies are preferably used. Humanized forms of non human (e.g., murine) antibodies are genetically engineered chimeric antibodies or antibody fragments having—preferably minimal—portions derived from non human antibodies. Humanized antibodies include antibodies in which complementary determining regions of a human antibody (recipient antibody) are replaced by residues from a complementarity determining region of a non human species (donor antibody) such as mouse, rat or rabbit having the desired functionality. In some instances, Fv framework residues of the human antibody are replaced by corresponding non human residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596).

Methods for humanizing non human antibodies are well known in the art. Generally, a humanized antibody has one or more amino acid residues introduced into it from a source which is non human. These non human amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a non human species. In practice, humanized antibodies may be typically human antibodies in which some complementarity determining region residues and possibly some framework residues are substituted by residues from analogous sites in rodent antibodies.

Human antibodies can also be produced using various techniques known in the art, including phage display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147: 86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368: 812-13; Fishwild et al., 1996. Nature Biotechnology 14:845-

51; Neuberger, 1996. Nature Biotechnology 14:826; Lonberg and Huszar, 1995. Intern. Rev. Immunol. 13:65-93).

In order to identify putative agents capable of specifically regulating MMP-9, an agent may be assessed regarding its capability of interacting with the OG domain of MMP-9.

Thus, according to an aspect of the invention, there is provided a method to determine whether an agent is a specific regulator of MMP-9 comprising determining whether the agent is capable of interacting with an OG domain of MMP-9, the agent being a putative MMP-9 specific regulator.

Through meticulous experimentation, the present inventors have uncovered the 3D structure of full-length pro-MMP-9. The complete MMP-9 3D structure described herein may be used in the rational design of drugs which modulate (preferably inhibit) the action of MMP9. These MMP9 modulators may be used to prevent or treat the undesirable physical and pharmacological properties of MMP9 activity. Thus, according to one embodiment of this aspect of the invention, an agent may be assessed for its ability to specifically regulate MMP-9 by comparing its structure with the structure of the MMP-9 OG domain. This may be performed by using computer models of the full length MMP-9 such as those generated by the present inventors with the aid of programs such as GASBOR and CHADD. This method may be particularly suitable for identifying peptide agents and small molecules.

Once the structure of the agent is at hand one can design peptides which fit into the 3D structure of the OG domain and hopefully stanilize or disrupt it. Such peptides/small molecule can be screened for specifically binding the OG domain.

Generation of peptide mimetics, as described hereinabove, may be effected using various approaches, including, for example, display techniques.

Methods of constructing such display libraries are well known in the art. Such methods are described in, for example, Young A C, et al., "The three-dimensional structures of a polysaccharide binding antibody to *Cryptococcus neoformans* and its complex with a peptide from a phage display library: implications for the identification of peptide mimotopes" J Mol Biol 1997 Dec. 12; 274(4):622-34; Giebel L B et al. "Screening of cyclic peptide phage libraries identifies ligands that bind streptavidin with high affinities" Biochemistry 1995 Nov. 28; 34(47):15430-5; Davies E L et al., "Selection of specific phage-display antibodies using libraries derived from chicken immunoglobulin genes" J Immunol Methods 1995 Oct. 12; 186(1):125-35; Jones C R T al. "Current trends in molecular recognition and bioseparation" J Chromatogr A 1995 Jul. 14; 707(1):3-22; Deng S J et al. "Basis for selection of improved carbohydrate-binding single-chain antibodies from synthetic gene libraries" Proc Natl Acad Sci USA 1995 May 23; 92(11):4992-6; and Deng S J et al. "Selection of antibody single-chain variable fragments with improved carbohydrate binding by phage display" J Biol Chem 1994 Apr. 1; 269(13):9533-8, which are incorporated herein by reference.

Peptide mimetics can also be uncovered using computational biology. For example, various compounds can be computationally analyzed for an ability to bind OG domain using a variety of three-dimensional computational tools as described in the Examples section herein below. Software programs useful for displaying three-dimensional structural models, such as RIBBONS (Carson, M., 1997. Methods in Enzymology 277, 25), O (Jones, T A. et al., 1991. Acta Crystallogr. A47, 110), DINO (DINO: Visualizing Structural Biology (2001) www.dino3d.org); and QUANTA, INSIGHT, SYBYL, MACROMODE, ICM, MOLMOL, RASMOL and GRASP (reviewed in Kraulis, J., 1991. Appl Crystallogr. 24, 946) can be utilized to model interactions between the OG domain and prospective peptide mimetics to thereby identify peptides which display the highest probability of binding to the OG region. Computational modeling of protein-peptide interactions has been successfully used in rational drug design, for further detail, see Lam et al., 1994. Science 263, 380; Wlodawer et al., 1993. Ann Rev Biochem. 62, 543; Appelt, 1993. Perspectives in Drug Discovery and Design 1, 23; Erickson, 1993. Perspectives in Drug Discovery and Design 1, 109, and Mauro M J. et al., 2002. J Clin Oncol. 20, 325-34.

According to another embodiment of this aspect of the invention, an agent may be assessed for its ability to specifically regulate MMP-9 by incubating the agent with isolated MMP-9. Since the amino acid sequence of MMP-9 is known, the isolated MMP-9, or fragment thereof which comprises the OG domain may be generated using standard recombinant DNA technology or by chemical synthesis. Standard protein labeling techniques may be used for assaying binding of the agent to the target. Labeling may be direct (e.g., by S35 labeling of the MMP-9) or indirectly, such as by the use of secondary antibodies. Standard immunological (ELISA, imunoprecipitation) and biochemical (e.g., gel filtration) methods can be used for assassing agent binding.

Once putatuive agents are identified, they may be assayed for their abilities to regulate MMP-9 functions and for their ability to be selective towards MMP-9. An example of such an assay is the in-situ zymographic analysis of collagenolytic activity described in Example 7 herein below.

As mentioned, MMP-9 is known to be a prototypical target in inflammatory diseases, because of its tissue-damaging roles and inflammation-promoting processing of soluble proteins, including protease inhibitors, chemokines and cytokines. Therefore, agents capable of down-regulating activities of MMP-9 may be used to treat MMP-9 related disorders.

Thus, according to an aspect of the invention, there is provided a method of treating a MMP-9 mediated medical condition, the method comprising administering to a subject in need thereof a therapeutically effective amount of an agent which specifically interacts with an OG domain of MMP-9, thereby treating the MMP-9 mediated medical condition.

As used herein the term "subject in need thereof" refers to a mammal, preferably a human subject.

As used herein the term "treating" refers to preventing, curing, reversing, attenuating, alleviating, minimizing, suppressing or halting the deleterious effects of an MMP-9 mediated disease or condition.

The phrase "MMP-9 mediated medical condition" refers to a disease or disorder in which MMP-9 may be attributed to its onset or progression. An example of an MMP-9 mediated medical condition is cancer, e.g. metastatic cancer such as breast, ovarian, bone, lung, pancreatic and prostate cancer.

In addition to playing a role in cancer, MMP-9 may be involved in other pathologies, for example, in arthritis or in neurodegenerative diseases such as multiple sclerosis (Firestein, Curr. Opin. Rheumatol. 4:348-354 (1992); Gijbels et al., J. Neuroimmunol. 41:29-34 (1992)). For example, high levels of MMP-9 have been detected in serum and synovial fluid of patients with inflammatory arthritis such as rheumatoid arthritis compared to healthy patients or patients with osteoarthritis (Ahrens et al., Arthritis & Rheumatism 39:1576-87 (1996); Gruber et al., Clin. Immunol. & Immunopathol., 78:161-171 (1996)). In addition, a correlation has been reported between the arthritic activity score of a joint and the amount of MMP-9 in the aspirated synovial fluid (Koolwijk et al. J. Reumatology, 22:385-393 (1995)).

Expression of MMP-9 is also detected in diseases of the nervous system. For example, prominent expression of MMP-9 has been found in reactive astrocytes and macrophages in demyelinating lesions compared to normal brain tissue (Cuzner et al., J. Neuropathol. Exp. Neurol, 55:1194-1204 (1996)). MMP-9 is elevated in encephelomyelitis (Gijbels, et al., J. Neuro. Res. 36:432-440 (1993); Proost, et al., Biochem, Biophys, Res. Comm. 192:1175-1181 (1993)), in the cerebrospinal fluid of patients with multiple sclerosis (Leppert, et al., Brain 121:2327-2334 (1998); Rosenberg et al., Brain Res., 703:151-155(1995)), and in patients with AIDS-related dementia (Conant, et al., Annals of Neurology 46: 391-398 (1999)). Furthermore, in patients with amyotrophic lateral sclerosis, MMP-9 expression is found in the pyramidal neurons of the motor cortex and in the motor neurons of the spinal cord (Lim et al., J. Neurochem., 67:251-259 (1996)).

MMP-9 has also been associated with a variety of other inflammatory diseases. For example, a high level of MMP-9 activity is found in the vessel wall of aortic aneurysms (Freestone, et al. Arteriosclerosis, Thrombosis & Vascular Biology, 15:1145-1151 (1995); Newman et al., Connective Tissue Research, 30:265-276, (1994); Sakalihasan et al., J. Vascular Surgery, 24:127-33 (1996)). In addition, patients with giant cell arteritis have increased levels of MMP-9, and MMP-9 mRNA is found in smooth muscle cells and fibroblasts in the regions of fragmented elastic tissue in the lamina media of inflamed vessels (Sorbi, et al., Arthitis & Rheumatism, 35:1747-1753 (1996)). Increased levels of MMP-9 are also found in sputum of patients with cystic fibrosis and in bronchoalveolar lavage fluids of those with bronchiectasis (Delacourt et al., Amer. J. Respiratory & Critical Care Med., 152: 765-764 (1995); Sepper et al, Chest, 106:1129-1133 (1994)). High levels of MMP-9 have also been found in blister fluids from the skin lesions of bullous pemphigoid patients (Stahle-Backdahl et al., J. Clinical Invest., 93:2022-2030 (1994)).

MMP-9 expression has also been implicated in the pathogenesis of several other diseases. For example, MMP-9 has been implicated in polycystic kidney disease (Murray et al., Conn. Tissue Res., 33:249-256 (1996)), membranous nephropathy (McMillin et al., J. Clin. Invest., 97:1094-1101 (1996)), and Alzheimer's disease (Lim et al., J. Neurochem., 68:1606-1611 (1997)).

Accordingly, the present invention contemplates the treatment of all the above referred to diseases or conditions using agents capable of selectively interacting with the OG domain of MMP-9.

The agents of the present invention can be administered to the subject per se, or as part of a pharmaceutical composition, which also includes a physiologically acceptable carrier. The purpose of a pharmaceutical composition is to facilitate administration of the active ingredient to an organism.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the agent accountable for the intended biological effect i.e. down-regulation of an activity of MMP-9.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media [Mutter et al. (1979)].

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Expression of MMP-9: Recombinant pro-MMP-9 was expressed by infection of Sf9 insect cells with a baculovirus carrying the cDNA of human proMMP-9 [19]. Liter quantities of cell culture fluids were centrifuged, filtered and purified to homogeneity by gelatin-Sepharose chromatography [52]. The material was extensively dialyzed in 100 mM Tris pH 7.4, 100 mM NaCl, 10 mM $CaCl_2$ (buffer C) before further processing and about 20 mg were used in the present study. A mutant lacking the OG-domain (MMP-9ΔOG) was prepared in a similar way [19].

Small Angle X-ray Scattering: SAXS experiments in solution were performed at station 2.1 [53] of the Synchrotron Radiation Source, Daresbury Laboratory, UK, following standard procedures. The protein solution was centrifuged for 5 min at 13,000×g before being measured at 4° C. Scattering curves were collected with a two-dimensional multiwire proportional counter, at sample-to-detector distances of 1 m (7 mg/ml, 100 μl) and 4.25 m (0.8, 1.6, 2.5 mg/ml, 100 μl), at a wavelength (λ) of 1.54 Å, covering the momentum transfer range $0.008 < q < 0.78$ Å$^{-1}$ ($q = 4\pi \sin \theta / \lambda$, where 2θ is the scattering angle). The data were collected in 30 successive 1 minute frames, and then normalized to the intensity of the incident beam, radially integrated over a 60° sector, averaged over the frame number and normalized to the detector response. The scattering of the buffer was then subtracted and the low- and high-angle curves were merged over the q range of 0.05-0.15 Å$^{-1}$. Reproducibility of the intensity as a function of time was evidence for lack of radiation damage of the monomeric pro-MMP-9 sample. The radius of gyration ($R_g$) was evaluated using the Guinier approximation: $I(q) = I(0) \exp(-q^2 R_g^2 / 3)$ for $qR_g < 1.3$ [54], and also from the entire scattering curve with the indirect Fourier-transform program GNOM [55]. GNOM also provides the distance distribution function p(r) of the particle and its maximum dimension $D_{max}$, defined as the point where p(r) becomes zero. To determine p(r), p(0)=0 and p($D_{max}$) were assigned free, in the first instance, to judge whether the chosen r interval was correct. $D_{max}$ was the lowest value yielding the lowest positive p($D_{max}$). After fixing $D_{max}$, p(0) and p($D_{max}$) were fixed to zero. The data was then cut at the low and high angle region until the p(r) functions converged.

The crystal structures of the two MMP-9 domains (N-terminal catalytic domain and C-terminal hemopexin-like domain) were analyzed using the program CRYSOL [36] in order to calculate their corresponding theoretical scattering curves. These were further Fourier-transformed to yield their theoretical pair distribution functions, while the $D_{max}$ and $R_g$ values were calculated. Ab initio modeling of the SAXS curves are described in detail below. Structural figures were made with PyMOL (DeLano, W. L. The PyMOL Molecular Graphics System (2002) DeLano Scientific, San Carlos, Calif., USA. www.pymol.org).

To further confirm the accuracy of the model, its solution hydrodynamic properties were calculated using HYDROPRO [34], and then compared to the experimental values. The radius of shell minibeads was varied from 2.2 to 4.2 Å in six increments. The solvent density and viscosity, and the protein partial specific volume were calculated using SEDNTERP [27]. Sphere radii for the hydrodynamic shell model varied between 3.8 to 5.3 Å. The radius of the dummy residues (DRs) in the SAXS model is 3.8 Å. However, the actual dimension of the shell model is slightly bigger due to protein hydration, yet the extent of enlargement is difficult to determine [34]. It was previously suggested that increasing the DRs radius by 1.5 Å would take into account hydration reliably [56].

Atomic Force Microscope imaging: Imaging was performed using a Multimode atomic force microscope (MMAFM Veeco/Digital Instruments, Santa Barbara, Calif., USA) equipped with an E-scanner, with a maximum scan range of 14×14 μm². Samples were imaged in air or in buffer using Tapping Mode. To obtain samples free of artifacts from spurious adsorbates, mainly salt deposition, an aggressive rinsing procedure was required. By using the amine-modified silane surfaces and cross-linking procedure, it was possible to prepare surfaces that removed nearly all the background (as determined by blank runs), while maintaining significant surface concentration of protein.

In order to minimize the amount of force applied, the amplitude set point was adjusted to the maximum value that gave a stable trace. High-resolution images of biological samples in air were obtained using "spike" tips—DP14 "HI'REST™" probes from Mikromasch (Estonia). These probes have a resonant frequency of ca.160 kHz, a force constant of ca. 5 N/m, and a rated radius of curvature of 1 nm or less, but are only suitable for measurements on surfaces with rms roughness less than 20 nm due to the presence of additional "spikes" which could cause multiple contacts on a rough surface. DNP-S probes (Veeco) with nominal radius of 20 nm were used for the liquid measurements, which were performed in the standard MMAFM liquid cell. The sizes of the protein molecules were determined from cross-sectional analysis. The width values were than corrected for broadening by the tip, by subtracting the tip envelope as observed from a typical high resolution SEM image.

Size exclusion chromatography: The oligomeric mixture of pro-MMP-9 was loaded on a Superdex-200 column (300× 10 mm, Amersham Biosciences), pre-equilibrated and operated at 4° C. The sample volume was 100 µl of 1.1 mg/ml pro-MMP-9 and the flow rate was 0.5 ml/min. Elution was monitored by absorbance at 280 nm. The Stokes radius was determined by analysis of the elution time with respect to a calibration curve using both a Porath plot and a Laurent and Killander plot [Siegel, L. M., and Monty, K. J. (1966). Biochim Biophys Acta 112, 346-362]. The five standard proteins (Amersham Biosciences) of known Stokes radii used for the calibration curve were thyroglobulin (85 Å), ferritin (61 Å nm), catalase (52.2 Å), aldolase (48.1 Å), and albumin (35.5 Å). The void volume measured by blue dextran had a retention time, $t_0$ of 16.23 min and the total volume determined by vitamin B-12 had a retention time, $t_T$, of 39.44 min. From these values, the partition coefficient of a given protein, Kd, was calculated as: $Kd=(t_e-t_0)/(t_T-t_0)$, $t_e$ being the retention time of a given protein. Very similar results were obtained for both the Porath and Laurent and Killander plots. The uncertainties in retention times for three repeating sets of experiments were 0.5% on average. The linear least-square fits had a correlation coefficient of $r^2=0.97$ for both the Porath and Laurent and Killander plots.

Glycerol-gradient sedimentation: A sample (0.2 mg) of purified pro-MMP-9 was layered onto four polyallomer tubes containing 10-45% glycerol gradient (prepared in Gradient-Master BioComp™) in buffer. The tubes were then centrifuged in a SW41 rotor at 37,000 rpm, 63 h, 4° C. The gradient was then fractionated to 0.5 ml samples that were assayed for the presence of monomeric and other oligomeric structures by gelatin zymography [Masure, S., Proost, P., Van Damme, J., and Opdenakker, G. (1991). Eur J Biochem. 198, 391-398]. Fractions containing homogenous monomeric structures were pooled and dialyzed against buffer to remove excess glycerol. Protein concentration was determined using the BCA protein assay kit (Pierce).

Analytical ultracentrifugation: Sedimentation velocity experiments were performed in a Beckman Optima XL-A analytical ultracentrifugation equipped with An-50 Ti rotor. Experiments were carried at 20° C. in buffer C. A sample at a protein concentration of 0.4 mg/ml was loaded into 12 mm path cells and centrifuged at 50,000 rpm. Absorbance at 280 nm was recorded every 160 sec using 0.001 cm radial spacing over the radial range 6-7.3 cm.

The sedimentation profiles were analyzed using the software SEDFIT [Schuck, P. (2000). Biophys J. 78, 1606-1619] which allows evaluation of the sedimentation coefficient (s). The 130 experimental curves were analyzed and the distribution of the sedimentation coefficient, c(s), was obtained between 0.3 to 50 S at a resolution of 200 steps at this region, and grid size of 500 points. The confidence level for the parameterization was set to 0.9. The software SEDNTERP [Laue, T. M., Shah, B. D., Ridgeway, T. M., and Pelletier, S. L. (1992). Analytical Ultracentrifugation in Biochemistry and Polymer Science (Cambridge, U.K.: Royal Society of Chemistry)] was used to estimate the solvent density ($\rho$) to be 1.0062 gr/cm³, and the viscosity ($\eta$) to be 1.045 cP. The protein partial specific volume ($\bar{v}$) was calculated based on the amino acid and glycan composition to be 0.7328 cm³/gr, where the amino acid parameters by Kharakoz [Kharakoz, D. P. (1997). Biochemistry. 36, 10276-10285] were used.

Amine Functionalized Substrate Preparation for AFM imaging: These surfaces were selected for their high concentration of primary amine groups that interact with glutaraldehyde which cross-links and binds the protein. Glutaraldehyde forms an amide linkage to an amine surface group. The free amine of glutaraldehyde crosslinks the protein spontaneously by covalent interaction to amine groups ubiquitously present on the outer surface of the protein. Thus, there is no need for engineering or modification in order to affix the protein to the surface. Furthermore, this method only minimally perturbs the random distribution in protein conformation and orientation on the surface.

Preparation and characterization of the amine functionalized substrates used to specifically bind the protein (Veeco Metrology, Inc Santa Barbara, Calif. Part Number FSUB-11) is described briefly. Silicon chips of 1 cm² were diced from polished <111> wafers (International Wafer Servive INC.—Denmark). The silicon chip was modified with an amine terminated silane by plasma enhanced chemical vapor deposition ($4^{th}$ State, LLC, Belmont, Calif.) to create an amine functionalized substrate. The surface composition of the substrates was analyzed by X-ray Photoelectron Spectroscopy (XPS) using a Kratos Axis Ultra (Kratos, Manchester, UK) with a monochromated Al $k_\alpha$ x-ray source at 1486.6 eV both before and after amine functionalization. Amine groups, indicated by a nitrogen peak in the XPS spectra, were present at the surface only after the amine functionalization. Root mean square (RMS) surface roughness of the treated substrates was 1.8 Å as determined by Atomic Force Microscopy (AFM) applying tapping mode, in air with OTESPprobes (VEECO). A Horseradish Peroxidase (HRP) assay was used to determine the binding potential of the amine functionalized substrates. HRP labeled antibodies were immobilized to the amine functionalized substrate through a glutaraldehyde crosslinker. Substrates were sonicated to remove all unbound antibody and then analyzed with SureBlue Reserve TMB 1 Component Peroxidase Substrate (Kirkegaard and Perry Labs, Maryland). Binding activity was determined by reading absorbance at 450 nm.

Protein Immobilization Procedure: The aminized dies were kept in a desiccator at 4° C. Immediately before use, pro-MMP-9 was immobilized to the amine functionalized substrates through a glutaraldehyde crosslinker by the following procedure: 1.25% glutaraldehyde in 0.1 M Sodium Carbonate solution (pH 9) was incubated on the amine functionalized substrate overnight. The substrate was then rinsed thoroughly with sodium carbonate solution to remove unbound glutaraldehyde. Sample volume of 100 µl containing 0.1 mg/ml monodisperse solution of pro-MMP9ΔOG mutant or wild-type pro-MMP-9, fractionated to contain the monomeric form, were then incubated on the dies for 3 h. The samples were rinsed gently with 2×200 µl buffer followed by 5×200 µl Milli-Q water and finally dried under a stream of nitrogen. The glutaraldehyde served as covalent cross-linker of the protein to the aminized surface. This ensured robust attachment of the protein molecules to the surface during the rinsing and subsequent imaging. For AFM experiments run in buffer, the samples were kept hydrated continuously.

Ab Initio modeling of SAXS curves: The programs GASBOR [Svergun, D. I., Petoukhov, M. V., and Koch, M. H. (2001). Biophys J 80, 2946-2953] and CHADD [Petoukhov, M. V., Eady, N. A., Brown, K. A., and Svergun, D. I. (2002). Biophys J 83, 3113-3125] were used to generate low-resolution models. To take into account the glycosylations on pro-MMP-9 it was assumed that a single glycan is equivalent to ~1.6 amino acid residues according to its electronic density and length [Receveur, V., Czjzek, M., Schulein, M., Panine, P., and Henrissat, B. (2002). J Biol Chem. 277, 40887-40892]. It was also found that this value represents the relation between the averaged molecular weights of glycans and residues. The total number of DRs was than calculated, based on the amino acid sequence and the glycan composition that was previously characterized [Van den Steen, P. E., Van Aelst, I., Hvidberg, V., Piccard, H., Fiten, P., Jacobsen, C., Moestrup, S. K., Fry, S., Royle, L., Wormald, M. R., Wallis, R., Rudd, P. M., Dwek, R. A., and Opdenakker, G. (2006). J Biol Chem. 281, 18626-18637].

Several models of the same input parameters were generated for each method, in order to check for convergence of the model to a unique solution through the random Monte-Carlo fitting procedure. The models were inspected using DAMAVER [Volkov, V. V., and Svergun, D. I. (2003). Journal of Applied Crystallography 36, 860-864] in order to choose the most probable solution, and to compute averaged normalized spatial discrepancy (NSD) values (see Supplemental Data Results). The crystal structures of the terminal domains [Elkins, P. A., Ho, Y. S., Smith, W. W., Janson, C. A., D'Alessio, K. J., McQueney, M. S., Cummings, M. D., and Romanic, A. M. (2002). Acta Crystallogr D Biol Crystallogr 58, 1182-1192; Cha, H., Kopetzki, E., Huber, R., Lanzendorfer, M., and Brandstetter, H. (2002). J Mol Biol 320, 1065-1079] were then docked in the representative model using the software SUPCOMB [Kozin, M. B., and Svergun, D. I. (2001). Journal of Applied Crystallography 34, 33-41].

In-situ zymographic analysis of collagenolytic activity: In-situ zymography [Deshane, 2003] was performed by incubation of human fibrosrcoma HT1080 (CCL-121; ATCC, Rockville, Md.) cells with 60 nM anti-MMP9hr or corresponding buffer for control, and 450 nM labeled collagen (Oregon green-labeled collagen type-IV that is intramolecularly quenched—Molecular probes) at 37° C. for 16 h. The degradation of collagen gives rise to green fluorescence, which is indicative of net collagenolytic activity. Prior to imaging, the samples were stained with Hoechst 33258 (Molecular Probes) at a final concentration of 3.8 µg/ml for nuclear labeling. Samples were examined and photographed by fluorescence microscope (E600; Nikon, Tokyo, Japan) equipped with Plan Fluor objectives connected to a CCD camera (DMX1200F; Nikon). The experiment was repeated six times. Images were assembled using Adobe Photoshop (Adobe systems, San Jose, Calif.).

EXAMPLE 1

Isolation and Characterization of Pro-MMP-9 in its Monomeric Form

Molecular size and shape determination, structural reconstruction, and analysis of single molecule images of pro-MMP-9 monomers require monodispersed and homogeneous protein samples. The following example describes a combination of various methods to express, isolate and characterize the monomeric form of pro-MMP-9. Characterization of molecular radius was used to validate spectroscopic shape determination.

Results

Recombinant pro-MMP-9 was expressed and purified from baculovirus infected Sf9 cells as previously reported [19] (see Materials and Methods). This enzyme forms mixtures of monomers and other higher oligomeric species [20].

FIG. 1B shows the relative molecular ratio of pro-MMP-9 monomer to its oligomeric species as determined by analytical size exclusion chromatography (SEC). The main peak (No. 3) in the chromatogram comprises the pro-MMP-9 monomer with Stokes radius of 45.4 Å (see inset). The Stokes radius was determined based on the corresponding retention time using conventional procedures.

Isolation of pro-MMP-9 monomers from higher oligomeric species in preparative amounts was achieved by glycerol-gradient sedimentation [26]. FIG. 1C shows zymography analysis of the various fractions. The isolated monomer fraction was subjected to analytical ultracentrifugation (AUC) for additional estimation of its Stokes radius (FIG. 1D). In this sedimentation velocity experiment, a uniform pro-MMP-9 solution is subjected to a gravimetric field. This produces a depletion of solute near the meniscus and the formation of a sharp boundary between the depleted region and the uniform concentration of sedimenting solute (FIG. 1D, inset). The rate of movement of this boundary can be measured and leads to the determination of the sedimentation coefficients, which depends directly on the mass of the particles and inversely on the frictional ratio, which is in turn a measure of effective size and shape.

Pro-MMP-9 monomer was found to sediment as a single species with the main peak representing 91% of the total protein in the sample with a normalized sedimentation coefficient, $s°_{20,w}$, of 4.4 S (FIG. 1D). This value is compatible with a recent measurement [19]. A Stokes radius of 44.1 Å was computed by the program SEDNTERP [27] using a calculated partial specific volume of 0.7328 $cm^3/g$. AUC-based shape analysis (using the experimental frictional ratio) was indicative of elliptical shape with axial ratio a/b of 1:6. The molecular radial results obtained by AUC are consistent with the value obtained by SEC (45.4 Å). In addition, theoretical estimation of the radius, by SEDNTERP, using the pro-MMP-9 molecular mass and amino acid and glycan composition yielded a molecular equivalent spherical radius of 28.7 Å. Deviation of this value from the experimental Stokes radii provides another indication for a non-spherical shape, either elongated or incorporating cavities.

EXAMPLE 2

Molecular Shape Analysis of Pro-MMP-9 by Small-Angle X-ray Scattering (SAXS) Reveals an Elongated Three-Domain Structure Results The global conformation of pro-MMP-9 monomer in solution was investigated by SAXS. In SAXS, the scattering profile derives from the entire ensemble of randomly oriented molecules, yielding information about their averaged conformation (on the order of approximately a nanometer). SAXS thus differs from crystallographic structural analysis, which requires hard-to-get high quality crystals of macromolecules, and is one of a few structural techniques for studying proteins in solution. This method utilizes the elastic scattering of incident X-ray photons by the target molecule electrons. The electron density distribution, as governed by the arrangement of atoms in the molecule leads to an interference pattern. The three dimensional shape of the molecule is then reconstructed from the scattering profile [28].

Scattered intensity was observed over a momentum transfer range $0.008<q<0.46$ $Å^{-1}$ corresponding to a d-spacing range of $14<r<785$ Å (FIG. 2A). The lower value (14 Å) fixes the ultimate resolution obtainable in the measurements. The scattered intensities are linear in the small-q region (scattering profile see FIG. 2A) and are nicely fitted by the Guinier law. The slope was found to be weakly correlated with protein concentration. This means that neither aggregation nor inter-particle interference contribute significantly to the signal. The radius of gyration ($R_g$) resulting from the measurement is 50±2.7 Å. The function p(r) represents the distribution of interatomic distances within the molecule (pair distribution function—FIG. 2A, inset). Extraction of $R_g$ from p(r) gives a comparable value, 49.2 Å, indicating accurate preliminary data analysis (prior to the fitting procedure). The maximal interatomic distance ($D_{max}$) is 160 Å. The shape of p(r) is indicative of an elongated ellipsoid structure (see for example [29-31]).

The three dimensional reconstruction model of pro-MMP-9 was obtained using the programs GASBOR [32] and CHADD [33]. Theoretical scattering curves are simulated from three-dimensional arrangements of spherical centers (or dummy residues) representing protein residues, which combine to form the overall protein shape. The final protein shape is determined by iterative fitting of the simulated theoretical curves to the experimental data. The advantage of CHADD is in the use of a priori knowledge obtained from available crystal structure of isolated domains to introduce constrains in the data analysis procedures. In contrast, models produced by GASBOR are calculated without any a priori knowledge. A detailed comparison between CHADD and GASBOR is described in Example 3, herein below.

FIG. 2B shows the three-dimensional reconstructed structure of pro-MMP-9. The Stokes radius of the reconstructed structure of pro-MMP-9 was calculated using the program HYDROPRO [34]. This calculated radius ranges between 44.9 and 47.1 Å, which agrees with the measured values of 45.4 and 44.1 Å obtained by SEC and AUC, respectively. Furthermore, both the SAXS model and axial ratio parameter obtained by AUC, suggest an elongated shape. Hence, the reconstructed shape restored from the experimental SAXS profile is consistent with the measured hydrodynamic data obtained both by SEC and AUC.

The simulated curve fitting analysis of this structure is presented in FIG. 2A (gray curve). The location of the alpha carbon backbone of the pro-catalytic domain was used as a constraint in the structural reconstruction analysis while the OG and the hemopexin-like domains were reconstructed using CHADD. Finally, the crystal structures of the pro-catalytic [22] domain and the hemopexin-like domain [24] were sequentially docked to the contour density using the software SUPCOMB [35] (FIG. 2B). The remaining density belongs to the OG domain that separates the two terminal domains by ~30 Å. This value was further verified by calculating the theoretical p(r) curves based on the crystal structures of the isolated N-terminal and C-terminal domains using the software CRYSOL [36]. The calculated $D_{max}$ values for these domains are 80 Å and 50 Å, respectively. Subtracting these values from the experimental $D_{max}$ of full-length pro-MMP-9 (160 Å), provides further verification of the reconstructed structure where the terminal domains are separated by ~30 Å.

Inspecting the volumes occupied by the OG and hemopexin-like domains reveals that they are of similar volume. However, the calculated molecular weight of the OG domain, including the O-glycans, is about half of the hemopexin-like domain. Computational sequence analysis of the OG domain using PONDR [37] revealed that this region is significantly disordered relative to the other domains (FIG. 2C). Thus, despite its observed compact conformation, this proline-rich OG domain possesses a disordered structure of relatively low density. Therefore, the relatively bulky electron density of the OG domain, detected by SAXS, represents a range of conformations retained by this linker peptide in solution. This suggests that the OG linker domain is flexible. The structural modeling program RAPPER [38, 39] was used to model possible linker conformations that will fit the observed scattering profile and density map. Specifically, 8 out of 500 calculated conformers fit the SAXS model of the linker. Theoretical scattering curves were calculated (using the SAXS program CRYSOL [36]) for the overall pro-MMP-9 model structure. FIGS. 2D and 2E describes the best linker models that fit both the experimental scattering curve and the SAXS density map of pro-MMP-9. The OG linker appears to exhibit multiple putative unstructured conformations.

EXAMPLE 3

Comparison of Modeling Software for the Analysis of the SAXS Data

Results

The programs GASBOR [Svergun, D. I., Petoukhov, M. V., and Koch, M. H. (2001). Biophys J 80, 2946-2953] and CHADD [Petoukhov, M. V., Eady, N. A., Brown, K. A., and Svergun, D. I. (2002). Biophys J 83, 3113-3125] were used to generate a low-resolution model of pro-MMP-9. Both programs find a representation of the protein by a 3D arrangement of spherical scattering centers that reproduce the measured scattering curve. The advantage of CHADD is in the use of a priori knowledge of a portion of the Cα locations as determined by the crystal structure of isolated domains while the rest of the molecule is modeled, whereas GASBOR models the whole structure without the incorporation of a priori knowledge In each of the programs, several independent computations are compared to analyze the convergence of the solution structures.

Eight independent GASBOR runs converged to a unique solution of an elongated overall conformation where one end is of larger size and can harbor the crystal structure of the N-terminal domain whereas the other end assumes a disk-like shape that can accommodate the crystal structure of the C-terminal domain (FIG. 5A). The terminal domains were docked to the GASBOR model using the program SUPCOMB [Kozin, M. B., and Svergun, D. I. (2001). Journal of Applied Crystallography 34, 33-41]. The remaining density belongs to the OG domain that separates the terminal domains by 50 Å, taken as the OG domain length. The normalized spatial discrepancy (NSD) within the eight calculations ranged from 1.42 to 1.57. The NSD value is a measure of the similarity between the solution structures: a lower value corresponds to a better overlap. The NSD values were calculated using DAMAVER [Petoukhov, M. V., and Svergun, D. I. (2003). Journal of Applied Crystallography 36, 540-544], which is also capable of choosing the most probable solution ($\chi^2=1.38$) and to determine the outliers.

In an alternate modeling scheme, which makes use of known structural information, the full-length pro-MMP-9 structure was reconstructed using CHADD. Eleven independent runs were computed and showed NSD values of 1.59-1.75 with no outliers, suggesting convergence of the solutions toward a unique model. The most probable solution ($\chi^2=1.66$) is shown in FIG. 5B. The model indicates an elongated, three-domain structure that shows a large bimodal shape with disk-like domains connected by the relatively low-density OG domain. The crystal structures of the pro-catalytic domain and the hemopexin domains were sequentially docked to the contour density using the software SUPCOMB [Kozin, M. B., and Svergun, D. I. (2001). Journal of Applied Crystallography 34, 33-41]. The remaining density belongs to the OG domain that separates the two terminal domains by ~30 Å, a value that well agrees with the theoretical size of the OG domain as computed by CRYSOL.

The two structures obtained by two independent modeling algorithms are the result of convergence of several calculations to a unique solution. An NSD value of 1.68 was obtained for testing the similarity between the GASBOR and CHADD models, indicating good agreement between models. Although the GASB OR model is rather elongated (with OG domain of 50 Å as opposed to 30 Å) both models share very similar characteristics, i.e., two fairly globular domains connected by a linker (elliptic N-terminal and C-terminal hemopexin joined by the OG linker) resulting in an overall elongated structure composed from two fairly globular domains connected by a linker. The agreement of the size of the OG domain with the value computed by CRYSOL, and the similarity in overall shape to the AFM results led the present inventors to choose CHADD as a more reliable model.

EXAMPLE 4

Characterization of Shape and Domain Flexibility of Pro-MMP-9 by Single Molecule Imaging Results To further verify the SAXS analysis, the present inventors designed an experiment to directly visualize the shape of pro-MMP-9 and evaluate the molecular properties of its OG domain as predicted in FIGS. 2B and E. Specifically, the present inventors conducted single molecule imaging analysis of wild type and an OG-deleted mutant of pro-MMP-9 (pro-MMP-9ΔOG) using atomic force microscopy (AFM). Reproducible images of single pro-MMP-9 molecules (FIG. 3) were obtained by cross linking the protein samples to an amine-modified silanized layer on a Si(111) surface prior to AFM imaging.

Samples were imaged both under buffer solution, and in air (FIGS. 6A-C). Best images were obtained in semi-dry mode using a "spike" tip. FIGS. 3A-C show a single molecule image of wild type pro-MMP-9 immobilized on the modified Si(111) surface. Consistent with the reported SAXS analysis, the protein image possesses an elongated multi domain structure. The image cross-section (FIG. 3C) representing height versus width reveals two separated protein domains presumably connected by the OG linker. In contrast, the pro-MMP-9ΔOG mutant lacking the 64-residue OG domain exhibits rather spherical shape with unresolved domain separation (FIGS. 3D-F).

EXAMPLE 5

Choice of Conditions and Controls for Atomic Force Microscopy (AFM) Imaging of Pro-MMP-9

Results

Samples were imaged both under buffer solution, and in air. Although the former mode approximates physiological conditions, the quality of the images was poor (FIG. 6A). The poor quality of the images could arise from several factors: (1) The tips designed to be used for wet conditions had a significantly larger radius than the "spike" tips used in ambient conditions. (2) The fully hydrated sample may be softer and easier to distort under the tip pressure. (3) The binding of the protein to the surface may still allow some degree of motion under fully hydrated conditions. Therefore, in order to improve the image quality, ambient conditions were applied where the sample was rinsed and excess water was removed by 2-3 minutes of gentle nitrogen flow. This procedure likely leaves a thin hydration layer on the sample and is hence termed "semi-dry mode". To check the protein shape in the absence of any hydration layer, we applied thorough desiccation (FIG. 6B), which led to loss of fine features, contraction of the protein, and image noise in the cross-sections.

The main difficulty in these semi-dry measurements was to obtain samples free of artifacts from spurious adsorbates, mainly salt deposition. Aggressive rinsing procedures were required to remove those adsorbates, but also led to the removal of much of the protein. By using the amine-modified silane surfaces and cross-linking procedure, it was possible to prepare surfaces which removed nearly all the background (as determined by blank runs), while maintaining significant surface concentration of protein, similar to what is seen under fully hydrated conditions. Blanks (FIG. 6C) prepared by incubation under identical conditions as the samples, but with no pro-MMP-9 typically contain no more than one feature on a 1 $\mu m^2$ image. Comparison to the samples with pro-MMP-9 indicated that on average less than 5% of the observed features could have been artifacts due to debris or dried salt.

Statistical analysis of AFM images: Statistical analysis of height, width, and lobe-to-lobe distances were determined for wild type pro-MMP-9 and pro-MMP-9ΔOG. These data are displayed as histograms in FIGS. 4A-E and are summarized in Table 1, herein below. Most probable values are reported, since the presence of two subpopulations may impose a bias on the mean value. Standard deviation is reported between brackets. The values correspond to the wild type pro-MMP-9 (n=90) and pro-MMP-9ΔOG mutant (n=120). Lobe-to-lobe distances were measured between the peaks in the XZ cross-section. Values were extracted only if the orientation of the protein on the surface allowed identification of two distinct domains (n=83). The separation between lobes in pro-MMP-9ΔOG could not be distinguished.

TABLE 1

|  | Wild type | Pro-MMP-9ΔOG |
| --- | --- | --- |
| Height | 34 (7.5) | 22 (2.9) |
| Width | 190 (33) | 130 (13) |
| Lobe-to-lobe | 78 (9.5) | N/A |

The most probable height values were 34 Å and 22 Å, for the wild type and mutant respectively. Comparison to the possible height values extracted from the crystal structures [Elkins, P. A., Ho, Y. S., Smith, W. W., Janson, C. A., D'Alessio, K. J., McQueney, M. S., Cummings, M. D., and Romanic, A. M. (2002). Acta Crystallogr D Biol Crystallogr 58, 1182-1192; Cha, H., Kopetzki, E., Huber, R., Lanzendorfer, M., and Brandstetter, H. (2002). J Mol Biol 320, 1065-1079] suggest a flattening of the protein image, which could arise from interactions with the surface, or some compression of the structure under the AFM tip. The shape of the histogram of FIG. 4A reveals that the wild type protein is distributed into two subpopulations, as opposed to the OG-deleted mutant (FIG. 4B), which has a single peak in the distribution. The most probable width values were 190 Å and 130 Å for the wild type (FIG. 4C) and pro-MMP-9ΔOG (FIG. 4D), respectively. This difference indicates that the OG domain has a significant contribution to the width of the wild type protein.

Some of the spread in height and width values is expected to occur as a consequence of different binding configurations of the protein to the surface. Because the protein is not spherical, binding states with the major axis oriented at different angles with respect to the surface normal will lead to different maximum heights and widths as measured by AFM. Thus, the height would vary as the cosine of this angle, and the width as the sine.

The most probable lobe-to-lobe distance values were 78 Å for wild-type pro-MMP-9 (FIG. 4E). This distance compares favorably to lobe-to-lobe values obtained by SAXS. The range of possible values from the SAXS model is in the range of 75-87 Å, depending on the allowed orientations of the individual domains.

EXAMPLE 6

Single Molecule Imaging Statistical Analysis Coupled with SAXS Reveal Protein Domain Flexibility Mediated by OG Domain Results A striking feature contrasting the two enzyme species is that the spread in both width and height values for the wild type is significantly larger than for the mutant (FIGS. 4A-E). Such differences could arise from the additional degrees of freedom lent to the wild-type structure by the OG domain, as opposed to the mutant, where the two lobes are more confined. The heterogeneity of sizes results from two main variables: the different orientations of the protein on the surface and different protein conformations. As the mutant contains no OG domain, it has a reduced conformational heterogeneity, meaning the spread of values stems mainly from different orientations on the surface.

The effect of the OG domain on protein flexibility is clearly observed in FIG. 4E which reports measurements of lobe-to-lobe distances. The spread of distances ranges from 55-85 Å and can be divided to two subpopulations. Remarkably, these results support the existence of multiple enzyme conformations mediated by flexible molecular nature of the OG domain. FIG. 4F presents some possible models of various protein conformations based on the derived lobe-to-lobe distances. The lobe-to-lobe distances were allowed to vary within one standard deviation (9.5 Å). The various OG domain conformations presented in FIG. 4F were calculated using the structural modeling program RAPPER [38, 39].

Protein flexibility of pro-MMP-9, detected by this novel molecular analysis provides new molecular insights into the overall structure and dynamics of the enzyme, highlighting the structure-function uniqueness of pro-MMP-9 over other members of the MMP family, including gelatinase A/MMP-2 [21]. For instance, in collagenase-1/MMP-1, the flexibility of a much shorter linker region is further constrained by interactions between the hemopexin domain and the pro-domain [40]. Similarly, in MMP-2 the second blade of the hemopexin domain is linked to the fibronectin domain through a hydrogen bond (Morgunova et al. Science 1999).

EXAMPLE 7

The Role of Protein Domain Flexibility in Enzymatic Function of Pro-MMP-9

Results

MMP-9 is a secreted enzyme, and it is not clear how it is targeted to the right location and how its activity is controlled in the pericellular space [41]. Specifically, it is not clear what the roles of the various domains are in mediating effective protein-substrate and protein-protein interactions during catalysis. The full-length structure of pro-MMP-9 reported here introduces novel insights into the structure of this enzyme and to its apparent domain flexibility. In particularly, the reported results raise the possibility that the observed protein flexibility in MMP-9 is required to mediate its function.

The contribution of the OG domain was postulated in earlier work to be a spacer moiety that allows independent movement of the terminal domains [19, 42, 43]. Interestingly, a bioinformatics "BLAST" search [44, 45] of all available databases revealed that the OG domain in pro-MMP-9 is homologous to similar disordered domains in a number of cell surface associated and ECM binding proteins (see Table 2, herein below). The results reported in Table 2 lie above the default E-value threshold. Identity and similarity values are in percentage.

TABLE 2

| Protein name | Organism | Identity | Similarity |
| --- | --- | --- | --- |
| Anchor region of surface protein | Gram-positive cocci | 42 | 62 |
| Outer membrane receptor proteins, mostly Fe transport | Haemophilus influenzae | 43 | 51 |
| Hemoglobin-binding protein | Haemophilus influenzae | 42 | 50 |
| Cellulose-binding protein B | Eubacterium cellulosolvens | 45 | 52 |
| Collagen adhesion protein | Bacillus thuringiensis serovar israelensis | 36 | 44 |

Remarkably, close structural homology was found between the OG linker and overall domain organization of pro-MMP-9 and the fungi cellulase [29, 31], for which the role of the linker in cellulase was proposed to mediate protein-cellulose binding and enzyme migration in intact matrices. This suggests that pro-MMP-9 mediates its biological function and enzymatic activities by cell surface association and/or interactions with solid substrates (e.g. ECM). Recently, Owen et al. described TIMP-1-resistant MMP-9 activity at the cell surface of neutrophils [46]. One way to achieve tethering of the MMP-9 hemopexin domain to the cell might be through interactions of the MT6-MMP/TIMP-1 complex at the cell surface. The present data suggests that OG domain flexibility allows the N-terminus of MMP-9 to access complex substrate networks (e.g. collagen like molecules) in the pericellular environment. Stabilization of such protein-substrate interactions may be achieved by non specific protein-protein interactions mediated by the proline-rich sequences [47] residing in MMP-9 OG domain. In contrast, the hemopexin-like domain and the fibronectin domain in pro-MMP-9 were shown to stoichiometrically bind substrates with great affinity [48, 49]. This suggests that pro-MMP-9 mediates its catalytic activities via both specific and non-specific interactions with its substrates. In this molecular scenario the two terminal domains will provide substrate specificity while the OG flexible domain is used to destabilize, for example, the tertiary structure of collagen type substrates via weak nonspecific interactions.

Importantly, correct interaction with TIMP-1, LRP-1 and megalin requires OG domain involvement to achieve proper orientation of the hemopexin-like and catalytic domains [19]. The OG-deleted mutant showed decreased affinity to these molecules, suggesting the OG-domain is essential for regulating the bioavailability of active MMP-9. Although the single molecule imaging results indicate that the spacing between the terminal domains is not constant, the quasiglobular shape of the OG domain, as obtained by SAXS model reconstruction, assures minimal separation between the two domains, allowing binding of regulators to the C-terminal domain without steric hindrance from the N-terminal catalytic domain. Such domain flexibility is not observed for MMP-2. This may explain why MMP-9 can bind directly to LRP-1 while MMP-2 requires the formation of precursor complex with TIMP-2 [50] or with thrombospondin [51] to achieve effective binding to LRP-1.

In order to test the role of the OG domain in collagenolytic activity of MMP-9 in-situ inhibition assays were performed. Anti-MMP-9—hinge region was used (anti-MMP-9hr from three different vendors: Sigma, Chemicon and Abcam). This commercially available antibody was raised against a peptide within the OG domain. The substrate used was fluorescently-labeled type-IV collagen that shows increased fluorescence upon degradation. FIGS. 7A-B shows that the antibody down regulates collagenolytic activity, either by hindering the flexibility of the OG domain or by steric hindrance that disrupt enzyme-substrate contacts as shown by in-situ zymography.

Fluorescently labeled type-IV collagen was overlaid on the MMP-2/9-producing cells HT-1080. Both MMP-2 and MMP-9 that are produced by this cell line are capable of degrading collagen type-IV, however it was shown that more than 70% of the purified MMPs are MMP-9 that show 4-fold specific activity towards collagen type-IV with relation to MMP-2. The collagenolytic activity was examined at the periphery of the cells with (FIG. 7A) or without (FIG. 7B) anti-MMP-9hr. Upon the addition of anti-MMP-9hr the collagenolytic activity is more confined in comparison to the diffusive activity of the reference.

Taken together, it may be hypothesized that affecting the OG domain reduces the collagenolytic potency whereas the gelatinolytic activity is unaffected.

CONCLUSIONS

This work represents the first experimental structural determination of full-length human pro-MMP-9 revealed by novel combination of structural analyses. A combination of single molecule imaging and SAXS was utilized to derive a comprehensive molecular model providing structural and dynamic insights to this important enzyme. Remarkably, the present results demonstrate the presence of a flexible and unstructured OG domain bridging the catalytic enzyme core and the hemopexin domain. This structure endows pro-MMP-9 with unique domain architecture relative to other family members. Such structural exclusiveness may be utilized for the design of isoform selective inhibitors for MMP-9. The design of regulators for MMP-9 may be targeted at restricting its domain flexibility, which may block its pathological activity in specific disease states.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES

1. Stetler-Stevenson, W. G., Aznavoorian, S., and Liotta, L. A. (1993). Tumor cell interactions with the extracellular matrix during invasion and metastasis. Annu Rev Cell Biol. 9, 541-573.
2. Werb, Z., and Chin, J. R. (1998). Extracellular matrix remodeling during morphogenesis. Ann N Y Acad Sci. 857, 110-118.
3. Wolf, K., Mazo, I., Leung, H., Engelke, K., von Andrian, U. H., Deryugina, E. I., Strongin, A. Y., Brocker, E. B., and Friedl, P. (2003). Compensation mechanism in tumor cell migration: mesenchymal-amoeboid transition after blocking of pericellular proteolysis. J Cell Biol. 160, 267-277.
4. Maskos, K. (2005). Crystal structures of MMPs in complex with physiological and pharmacological inhibitors. Biochimie 87, 249-263.
5. Agrawal, S., Anderson, P., Durbeej, M., van Rooijen, N., Ivars, F., Opdenakker, G., and Sorokin, L. M. (2006). Dystroglycan is selectively cleaved at the parenchymal basement membrane at sites of leukocyte extravasation in experimental autoimmune encephalomyelitis. J Exp Med. 203, 1007-1019.
6. Liu, Z., Shipley, J. M., Vu, T. H., Zhou, X., Diaz, L. A., Werb, Z., and Senior, R. M. (1998). Gelatinase B-deficient mice are resistant to experimental bullous pemphigoid. J Exp Med. 188, 475-482.
7. Opdenakker, G., Nelissen, I., and Van Damme, J. (2003). Functional roles and therapeutic targeting of gelatinase B and chemokines in multiple sclerosis. Lancet Neurol. 2, 747-756.
8. Van den Steen, P. E., Proost, P., Brand, D. D., Kang, A. H., Van Damme, J., and Opdenakker, G. (2004). Generation of glycosylated remnant epitopes from human collagen type II by gelatinase B. Biochemistry 43, 10809-10816.
9. Liu, Z., Zhou, X., Shapiro, S. D., Shipley, J. M., Twining, S. S., Diaz, L. A., Senior, R. M., and Werb, Z. (2000). The serpin alpha1-proteinase inhibitor is a critical substrate for gelatinase B/MMP-9 in vivo. Cell. 102, 647-655.
10. Van den Steen, P. E., Proost, P., Wuyts, A., Van Damme, J., and Opdenakker, G. (2000). Neutrophil gelatinase B potentiates interleukin-8 tenfold by aminoterminal processing, whereas it degrades CTAP-III, PF-4, and GRO-alpha and leaves RANTES and MCP-2 intact. Blood. 96, 2673-2681.
11. Heissig, B., Hattori, K., Dias, S., Friedrich, M., Ferris, B., Hackett, N. R., Crystal, R. G., Besmer, P., Lyden, D., Moore, M. A., Werb, Z., and Rafii, S. (2002). Recruitment of stem and progenitor cells from the bone marrow niche requires MMP-9 mediated release of kit-ligand. Cell. 109, 625-637.
12. Nelissen, I., Martens, E., Van den Steen, P. E., Proost, P., Ronsse, I., and Opdenakker, G. (2003). Gelatinase B/matrix metalloproteinase-9 cleaves interferon-beta and is a target for immunotherapy. Brain. 126, 1371-1381.

13. Yu, Q., and Stamenkovic, I. (2000). Cell surface-localized matrix metalloproteinase-9 proteolytically activates TGF-beta and promotes tumor invasion and angiogenesis. Genes Dev. 14, 163-176.
14. McQuibban, G. A., Gong, J. H., Tam, E. M., McCulloch, C. A., Clark-Lewis, I., and Overall, C. M. (2000). Inflammation dampened by gelatinase A cleavage of monocyte chemoattractant protein-3. Science 289, 1202-1206.
15. Monaco, S., Sparano, V., Gioia, M., Sbardella, D., Di Pierro, D., Marini, S., and Coletta, M. (2006). Enzymatic processing of collagen IV by MMP-2 (gelatinase A) affects neutrophil migration and it is modulated by extracatalytic domains. Protein Sci 15, 2805-2815.
16. Itoh, T., Matsuda, H., Tanioka, M., Kuwabara, K., Itohara, S., and Suzuki, R. (2002). The role of matrix metalloproteinase-2 and matrix metalloproteinase-9 in antibody-induced arthritis. J Immunol 169, 2643-2647.
17. Garg, P., Rojas, M., Ravi, A., Bockbrader, K., Epstein, S., Vijay-Kumar, M., Gewirtz, A. T., Merlin, D., and Sitaraman, S. V. (2006). Selective ablation of matrix metalloproteinase-2 exacerbates experimental colitis: contrasting role of gelatinases in the pathogenesis of colitis. J Immunol 177, 4103-4112.
18. Opdenakker, G., Van den Steen, P. E., and Van Damme, J. (2001). Gelatinase B: a tuner and amplifier of immune functions. Trends Immunol. 22, 571-579.
19. Van den Steen, P. E., Van Aelst, I., Hvidberg, V., Piccard, H., Fiten, P., Jacobsen, C., Moestrup, S. K., Fry, S., Royle, L., Wormald, M. R., Wallis, R., Rudd, P. M., Dwek, R. A., and Opdenakker, G. (2006). The hemopexin and O-glycosylated domains tune gelatinase B/MMP-9 bioavailability via inhibition and binding to cargo receptors. J Biol Chem. 281, 18626-18637.
20. Wilhelm, S. M., Collier, I. E., Marmer, B. L., Eisen, A. Z., Grant, G. A., and Goldberg, G. I. (1989). SV40-transformed human lung fibroblasts secrete a 92-kDa type IV collagenase which is identical to that secreted by normal human macrophages. J Biol Chem 264, 17213-17221.
21. Morgunova, E., Tuuttila, A., Bergmann, U., Isupov, M., Lindqvist, Y., Schneider, G., and Tryggvason, K. (1999). Structure of human pro-matrix metalloproteinase-2: activation mechanism revealed. Science. 284, 1667-1670.
22. Elkins, P. A., Ho, Y. S., Smith, W. W., Janson, C. A., D'Alessio, K. J., McQueney, M. S., Cummings, M. D., and Romanic, A. M. (2002). Structure of the C-terminally truncated human ProMMP9, a gelatin-binding matrix metalloproteinase. Acta Crystallogr D Biol Crystallogr 58, 1182-1192.
23. Stocker, W., and Bode, W. (1995). Structural features of a superfamily of zinc-endopeptidases: the metzincins. Curr Opin Struct Biol. 5, 383-390.
24. Cha, H., Kopetzki, E., Huber, R., Lanzendorfer, M., and Brandstetter, H. (2002). Structural basis of the adaptive molecular recognition by MMP9. J Mol Biol 320, 1065-1079.
25. Van den Steen, P. E., Opdenakker, G., Wormald, M. R., Dwek, R. A., and Rudd, P. M. (2001). Matrix remodelling enzymes, the protease cascade and glycosylation. Biochim Biophys Acta 1528, 61-73.
26. Olson, M. W., Bernardo, M. M., Pietila, M., Gervasi, D. C., Toth, M., Kotra, L. P., Massova, I., Mobashery, S., and Fridman, R. (2000). Characterization of the monomeric and dimeric forms of latent and active matrix metalloproteinase-9. Differential rates for activation by stromelysin 1. J. Biol. Chem. 275, 2661-2668.
27. Laue, T. M., Shah, B. D., Ridgeway, T. M., and Pelletier, S. L. (1992). Analytical Ultracentrifugation in Biochemistry and Polymer Science (Cambridge, U.K.: Royal Society of Chemistry).
28. Svergun, D. I., and Koch, M. H. (2002). Advances in structure analysis using small-angle scattering in solution. Curr Opin Struct Biol 12, 654-660.
29. Receveur, V., Czjzek, M., Schulein, M., Panine, P., and Henrissat, B. (2002). Dimension, shape, and conformational flexibility of a two domain fungal cellulase in solution probed by small angle X-ray scattering. J Biol Chem. 277, 40887-40892.
30. Violot, S., Aghajari, N., Czjzek, M., Feller, G., Sonan, G. K., Gouet, P., Gerday, C., Haser, R., and Receveur-Brechot, V. (2005). Structure of a full length psychrophilic cellulase from Pseudoalteromonas haloplanktis revealed by X-ray diffraction and small angle X-ray scattering. J Mol Biol. 348, 1211-1224.
31. von Ossowski, I., Eaton, J. T., Czjzek, M., Perkins, S. J., Frandsen, T. P., Schulein, M., Panine, P., Henrissat, B., and Receveur-Brechot, V. (2005). Protein disorder: conformational distribution of the flexible linker in a chimeric double cellulase. Biophys J. 88, 2823-2832.
32. Svergun, D. I., Petoukhov, M. V., and Koch, M. H. (2001). Determination of domain structure of proteins from X-ray solution scattering. Biophys J 80, 2946-2953.
33. Petoukhov, M. V., Eady, N. A., Brown, K. A., and Svergun, D. I. (2002). Addition of missing loops and domains to protein models by x-ray solution scattering. Biophys J 83, 3113-3125.
34. Garcia De La Torre, J., Huertas, M. L., and Carrasco, B. (2000). Calculation of hydrodynamic properties of globular proteins from their atomic-level structure. Biophys J. 78, 719-730.
35. Kozin, M. B., and Svergun, D. I. (2001). Automated matching of high- and low-resolution structural models. Journal of Applied Crystallography 34, 33-41.
36. Svergun, D., Barberato, C., and Koch, M. H. J. (1995). CRYSOL—A program to evaluate x-ray solution scattering of biological macromolecules from atomic coordinates. Journal of Applied Crystallography 28, 768-773.
37. Li, X., Romero, P., Rani, M., Dunker, A. K., and Obradovic, Z. (1999). Predicting protein disorder for N-, C-, and internal regions. Genome Informatics 10, 30-40.
38. DePristo, M. A., de Bakker, P. I., Lovell, S. C., and Blundell, T. L. (2003). Ab initio construction of polypeptide fragments: efficient generation of accurate, representative ensembles. Proteins. 51, 41-55.
39. DePristo, M. A., De Bakker, P. I., Shetty, R. P., and Blundell, T. L. (2003). Discrete restraint-based protein modeling and the Calpha-trace problem. Protein Sci. 12, 2032-2046.
40. Lauer-Fields, J. L., Juska, D., and Fields, G. B. (2002). Matrix metalloproteinases and collagen catabolism. Biopolymers. 66, 19-32.
41. Fridman, R., Toth, M., Chvyrkova, I., Meroueh, S. O., and Mobashery, S. (2003). Cell surface association of matrix metalloproteinase-9 (gelatinase B). Cancer Metastasis Rev. 22, 153-166.
42. Overall, C. M. (2002). Molecular determinants of metalloproteinase substrate specificity: matrix metalloproteinase substrate binding domains, modules, and exosites. Mol Biotechnol 22, 51-86.
43. Rudd, P. M., Mattu, T. S., Masure, S., Bratt, T., Van den Steen, P. E., Wormald, M. R., Kuster, B., Harvey, D. J., Borregaard, N., Van Damme, J., Dwek, R. A., and Opdenakker, G. (1999). Glycosylation of natural human neutrophil gelatinase B and neutrophil gelatinase B-associated lipocalin. Biochemistry 38, 13937-13950.
44. Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic Acids Res. 25, 3389-3402.
45. Schaffer, A. A., Aravind, L., Madden, T. L., Shavirin, S., Spouge, J. L., Wolf, Y. I., Koonin, E. V., and Altschul, S. F. (2001). Improving the accuracy of PSI-BLAST protein database searches with composition-based statistics and other refinements. Nucleic Acids Res. 29, 2994-3005.
46. Owen, C. A., Hu, Z., Barrick, B., and Shapiro, S. D. (2003). Inducible expression of tissue inhibitor of metalloproteinases-resistant matrix metalloproteinase-9 on the cell surface of neutrophils. Am J Respir Cell Mol Biol. 29, 283-294.
47. Williamson, M. P. (1994). The structure and function of proline-rich regions in proteins. Biochem J. 297, 249-260.
48. Collier, I. E., Krasnov, P. A., Strongin, A. Y., Birkedal-Hansen, H., and Goldberg, G. I. (1992). Alanine scanning mutagenesis and functional analysis of the fibronectin-like collagen-binding domain from human 92-kDa type IV collagenase. J Biol Chem. 267, 6776-6781.
49. Roeb, E., Schleinkofer, K., Kernebeck, T., Potsch, S., Jansen, B., Behrmann, I., Matern, S., and Grotzinger, J. (2002). The matrix metalloproteinase 9 (mmp-9) hemopexin domain is a novel gelatin binding domain and acts as an antagonist. J Biol Chem. 277, 50326-50332.
50. Emonard, H., Bellon, G., Troeberg, L., Berton, A., Robinet, A., Henriet, P., Marbaix, E., Kirkegaard, K., Patthy, L., Eeckhout, Y., Nagase, H., Hornebeck, W., and Courtoy, P. J. (2004). Low density lipoprotein receptor-related protein mediates endocytic clearance of pro-MMP-2.TIMP-2 complex through a thrombospondin-independent mechanism. J Biol Chem 279, 54944-54951.
51. Yang, Z., Strickland, D. K., and Bornstein, P. (2001). Extracellular matrix metalloproteinase 2 levels are regulated by the low density lipoprotein-related scavenger receptor and thrombospondin 2. J Biol Chem 276, 8403-8408.
52. Masure, S., Proost, P., Van Damme, J., and Opdenakker, G. (1991). Purification and identification of 91-kDa neutrophil gelatinase. Release by the activating peptide interleukin-8. Eur J Biochem. 198, 391-398.
53. Towns-Andrews, E., Berry, A., Bordas, J., Mant, G. R., Murray, P. K., Roberts, K., Sumner, I., Worgan, J. S., Lewis, R., and A., G. (1989). Time-resolved X-ray-diffraction station—X-ray optics, detectors, and data acquisition. Rev Sci Instrum 60, 2346-2349.
54. Guinier, A., and Fournet, G. (1955). Small-angle scattering of X-rays (New York: John Wiley & Sons, Inc.).
55. Svergun, D. I. (1992). Determination of the Regularization Parameter in Indirect-Transform Methods Using Perceptual Criteria. Journal of Applied Crystallography 25, 495-503.
56. Ackerman, C. J., Harnett, M. M., Harnett, W., Kelly, S. M., Svergun, D. I., and Byron, O. (2003). 19 A solution structure of the filarial nematode immunomodulatory protein, ES-62. Biophys J. 84, 489-500.
57. Siegel, L. M., and Monty, K. J. (1966). Determination of molecular weights and frictional ratios of proteins in impure systems by use of gel filtration and density gradient centrifugation. Application to crude preparations of sulfite and hydroxylamine reductases. Biochim Biophys Acta 112, 346-362.

What is claimed is:
1. A humanized antibody comprising an antigen recognition domain which specifically interact with an OG domain of MMP-9.
2. A pharmaceutical composition comprising as an active ingredient the molecule of claim 1 and a pharmaceutically acceptable carrier.

* * * * *